(12) United States Patent
Kumar et al.

(10) Patent No.: US 6,562,324 B1
(45) Date of Patent: May 13, 2003

(54) POLYMERS IN COSMETICS AND PERSONAL CARE PRODUCTS

(75) Inventors: Kanta Kumar, Maplewood, MN (US); Ramesh C. Kumar, Maplewood, MN (US); Smarajit Mitra, West St. Paul, MN (US)

(73) Assignee: Minnesota Mining and Manufacturing, St. Paul, MN (US)

( * ) Notice: Subject to any disclaimer, the term of this patent is extended or adjusted under 35 U.S.C. 154(b) by 0 days.

(21) Appl. No.: 08/460,958

(22) Filed: Jun. 5, 1995

Related U.S. Application Data

(60) Division of application No. 08/101,415, filed on Aug. 3, 1993, now Pat. No. 5,468,477, which is a continuation-in-part of application No. 07/881,946, filed on May 11, 1993, now abandoned.

(51) Int. Cl.[7] .......................... A61K 7/075; A61K 7/08; A61K 7/11; A61K 47/34
(52) U.S. Cl. .............................. 424/70.12; 424/70.122; 424/DIG. 2
(58) Field of Search ......................... 424/78.17, 70.12, 424/70.122, 70.2, DIG. 1, DIG. 2

(56) References Cited

U.S. PATENT DOCUMENTS

| | | | |
|---|---|---|---|
| 3,208,911 A | 9/1965 | Oppliger | 167/87 |
| 3,563,941 A | 2/1971 | Plueddemann | 260/28 |

(List continued on next page.)

FOREIGN PATENT DOCUMENTS

| | | |
|---|---|---|
| EP | 0 117 360 | 9/1984 |
| EP | 0 047 799 A2 | 1/1991 |
| EP | 0 408 311 | 1/1991 |
| EP | 0412704 | 2/1991 |
| EP | 0 412 704 | 2/1991 |
| EP | 0 412 707 | 2/1991 |
| EP | 0412710 | 2/1991 |
| EP | 0412770 | 2/1991 |
| EP | 0421588 | 4/1991 |
| WO | 93/23009 | 11/1993 |

OTHER PUBLICATIONS

Abstract—JP 56–092811 to Lion Corporation Dec. 27, 1979.
Abstract—JP 58113300; Jul. 6, 1983.
European Search Report for EP Appln. No. 99 12 1355.4 (May 9, 2001).

*Primary Examiner*—Edward J. Webman
(74) *Attorney, Agent, or Firm*—Finnegan, Henderson, Farabow, Garrett, & Dunner, L.L.P.

(57) ABSTRACT

Cosmetic compositions are provided containing vinyl-silicone graft or block copolymers of the formula

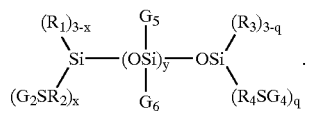

55 Claims, 1 Drawing Sheet

U.S. PATENT DOCUMENTS

| | | | |
|---|---|---|---|
| 3,641,239 A | 2/1972 | Mohrlok | 424/64 |
| 3,928,558 A | 12/1975 | Cheesman et al. | 424/47 |
| 3,957,970 A | 5/1976 | Korkis | 424/70 |
| 4,046,795 A | 9/1977 | Martin | 260/448 |
| 4,185,087 A | 1/1980 | Morlino | 424/70 |
| 4,238,393 A | 12/1980 | Takamizawa et al. | 260/22 |
| 4,268,499 A | 5/1981 | Keil | 424/68 |
| 4,311,695 A | 1/1982 | Starch | 424/184 |
| 4,479,893 A | 10/1984 | Hirota et al. | 252/542 |
| 4,532,132 A | 7/1985 | Keil | 514/772 |
| 4,563,347 A | 1/1986 | Starch | 424/70 |
| 4,654,161 A | 3/1987 | Kollmeier et al. | 252/74.15 |
| 4,724,851 A | 2/1988 | Cornwall et al. | 132/7 |
| 4,733,677 A | 3/1988 | Gee et al. | 132/7 |
| 4,744,978 A | 5/1988 | Homan et al. | 424/70 |
| 4,783,490 A | 11/1988 | Eckberg et al. | 522/99 |
| 4,839,167 A | 6/1989 | Yamamoto et al. | 424/71 |
| 4,902,499 A | 2/1990 | Bolich, Jr. et al. | |
| 4,971,786 A | 11/1990 | Grollier et al. | 424/47 |
| 4,987,180 A | 1/1991 | Obata et al. | 524/860 |
| 4,988,506 A | 1/1991 | Mitra et al. | 424/81 |
| 5,015,469 A | 5/1991 | Yoneyama et al. | |
| 5,032,460 A | 7/1991 | Kantner et al. | |
| 5,061,481 A | 10/1991 | Suzuki et al. | 424/63 |
| 5,078,988 A | 1/1992 | Lin et al. | |
| 5,079,313 A | 1/1992 | Okuno et al. | 525/487 |
| 5,202,190 A | 4/1993 | Kantner et al. | 428/447 |
| 5,278,228 A | 1/1994 | Matner et al. | 524/837 |
| 5,362,485 A * | 11/1994 | Hayama et al. | 424/70 |

* cited by examiner

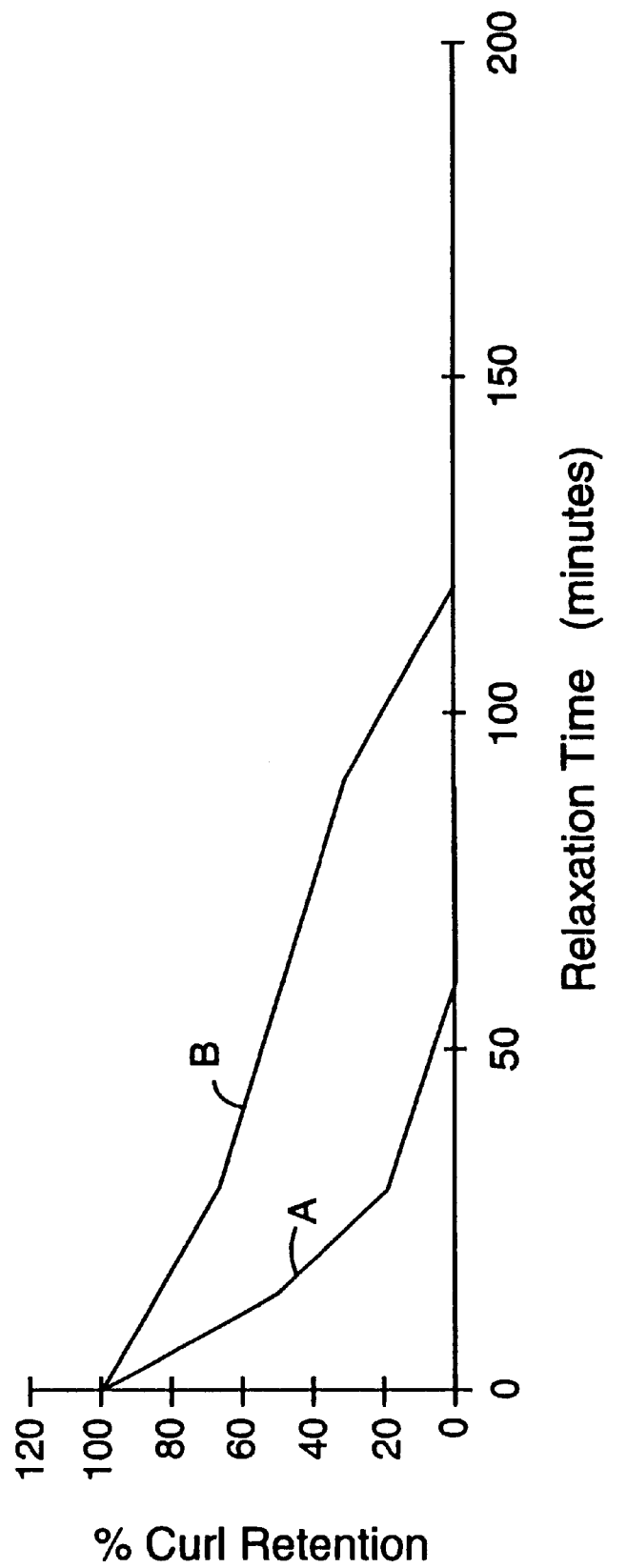

POLYMERS IN COSMETICS AND PERSONAL CARE PRODUCTS

RELATED APPLICATIONS

This application is a divisional application of U.S. Ser. No. 08/101,415, filed Aug. 3, 1993, now U.S. Pat. No. 5,468,477, which is a continuation-in-part application of U.S. Ser. No. 07/881,946, filed May 11, 1993, now abandoned.

TECHNICAL FIELD

The present invention relates to cosmetic compositions. More specifically, the present invention relates to cosmetic compositions containing a vinyl-silicone graft or block copolymer.

BACKGROUND OF THE INVENTION

Cosmetics are applied to skin, hair, teeth, and nails for the purpose of cleansing, and/or protecting these personal surfaces from noxious external influences, and to provide visual appeal to these surfaces. Keeping the body clean is surely the first and most primitive demand of personal hygiene and, therefore, one of the main purposes of cosmetics. Another purpose is to protect such personal surfaces. Cleansers protect the skin by removing impurities. Disinfectants protect the skin by destroying noxious bacteria and fungi. Other preparations act prophylactically by isolating the skin from contact with harmful external agents.

Typical skin protectors are applied before skin is exposed to harmful external agents. Ideally, such protectors act as an invisible sheath completely impenetrable to harmful agents or even deliver ingredients that kill harmful bacteria. Skin protectors can be differentiated according to their specific purposes, e.g., protection against chemical agents (caustic chemicals, detergent solutions, etc.); protection against dust and soil, tar, and lubricants; protection against physical agents (ultraviolet rays and heat); protection against mechanical injuries (lubricant and massage preparations) and insect repellents.

In addition to the above discussed purposes of basic cosmetics, the suppression of body odor or personal wetness is also a very important part of personal hygiene and therefor also a basic cosmetic function. Specific examples of such basic cosmetics are, e.g., soaps, detergents, cleansing lotions and the like for skin cleaning; shampoos, conditioners and the like for hair cleaning and protecting; toothpastes, tooth creams, and the like for oral hygiene; creams, emulsions, sunscreen preparations, sunburn preventive preparations, lubricating and massaging preparations, insect repellent preparations and the like to protect the skin from harmful effects of either chemicals, dust and soil, ultraviolet rays, insects, and other harmful agents present in the environment. Antiperspirant, foot deodorants, mouthwashes, and the like to improve or eliminate odors or personal wetness by eliminating bacterial actions, and/or retention of medicament on a surface are also within this category of basic cosmetic.

Another category of cosmetics is the "decorative products." Decorative products relate to the health of the skin only to the extent that they must damage it as little as possible. These products are used to hide small blemishes or symptoms of aging. They are also used to create a well-groomed appearance and to demonstrate the desire not to create a bad impression on the outside world. Decorative cosmetics may consist in surface measures, in which the preparation is applied to the surface of skin, nails, or hair, or in permanent measures that cannot be canceled by simple countermeasures. Their sole purpose is an alteration of the appearance, for example, preparation for coloring skin and nails, preparation for masking skin imperfections and shininess, hair grooming aids with and without lasting effects, and the like. Specific examples of decorative cosmetics useful to be applied to the face, also known as makeup cosmetics, include foundation, lipsticks, rouges, eyeliners, mascara, eyeshadows, eyebrow pencils, manicures, face powders, and the like. Cosmetics useful for application to the hair include hair oils, hair creams, hair lacquers, hair lotions, hair dyes and bleaches, permanent wave solutions, and the like. Skin-bleaching preparations, and hair-removal preparations are also considered decorative cosmetics because of their role in enhancing the appearance of the skin.

U.S. Pat. No. 3,563,941 to Plueddemann, published Feb. 16, 1971, discloses the preparation of silicone modified carnauba wax which is useful in cosmetic compositions. U.S. Pat. No. 3,641,239 to Mohrlok, issued Feb. 8, 1972, discloses the use of silicone wax in cosmetic formulations such as lipsticks. Silicone waxes, as defined, are organosiloxane copolymers containing carnauba wax, hydrocarbon, phenyl, or silphenylene groups in the silicone chain.

U.S. Pat. No. 4,268,499 to Keil, issued May 19, 1981, discloses antiperspirant emulsions containing polydiorganosiloxanes-polyoxyalkylene copolymers as well as volatile silicones. U.S. Pat. No. 4,532,132 to Keil, published Jul. 30, 1985, and U.S.

Pat. No. 4,311,695 to Starch, published Jan. 19, 1982, disclose the use of organosiloxane-polyoxyalkylene copolymers in skin care/personal care products.

Siloxanes (see, for example, U.S. Pat. No. 3,208,911 to Opplinger, issued Sep. 28, 1965) and siloxane-containing polymers have been taught also for their use in hair conditioning compositions. U.S. Pat. No. 4,902,499 to Bolich, Jr., et al., issued Feb. 20, 1990, describes the use of rigid silicone polymers in hair care compositions. U.S. Pat. No. 4,971,786 to Grollier et al., issued Nov. 20, 1990, describes the use of ethoxylated copolymer of dimethylsiloxane/3-hydroxy-propylmethylsiloxane in hair conditioning or shampoo/conditioner compositions. U.S. Pat. No. 4,839,167 to Yamamoto et al. issued Jun. 13, 1989, and U.S. Pat. No. 3,928,558 to Cheesman et al., issued Dec. 23, 1975, describes the use of a mixture of polyethersiloxane copolymers with a surfactant and water or water/ethanol soluble polymer in hair care application. U.S. Pat. No. 4,654,161 to Kollmeier et al., issued Mar. 31, 1987, describes organopoly-siloxanes containing betaine substituents. When used in hair care compositions, these compounds are said to provide good conditioning, compatibility with anionic components, hair substantivity, and low skin irritation. U.S. Pat. No. 4,563,347 to Starch, issued Jan. 7, 1986, relates to hair conditioning compositions which include siloxane components containing substituents to provide attachment to hair. Japanese Published Application 56-129,300 to Lion Corporation, published Oct. 9, 1981, relates to shampoo conditioner compositions which include an organopolysiloxane oxyalkylene copolymer together with an acrylic resin. U.S. Pat. No. 4,185,087 to Morlino, issued Jan. 22, 1980, describes quaternary nitrogen derivatives of trialkylamino hydroxy organosilicon compounds which are said to have superior hair conditioning properties. U.S. Pat. No. 4,479,893 to Hirota et al., issued Oct. 30, 1984, describes shampoo/conditioner compositions containing a phosphate ester surfactant and a silicon derivative (e.g., polyether- or alcohol-modified).

Polyether-modified polysiloxanes are also disclosed for use in shampoos in U.S. Pat. No. 3,957,970 to Korkis, issued May 18, 1976.

Siloxane-derived materials have also been used in hair styling compositions. U.S. Pat. No. 4,744,978 to Homan et al., issued May 17, 1988, describes hair styling compositions (such as hair sprays) which include the combination of a carboxy functional polydimethyl-siloxane and a cationic organic polymer containing amine or ammonium groups. Hair styling compositions which include polydiorganosiloxanes and a cationic organic polymer are taught in U.S. Pat. No. 4,733,677 to Gee et al., issued Mar. 29, 1988, and U.S. Pat. No. 4,724,851 to Cornwall et al., issued Feb. 16, 1988. Japanese Published Application 56-092,811 to Lion Corporation, published Dec. 27, 1979, describes hair setting composition which comprises an amphoteric acrylic resin, a polyoxyalkylene-denatured organopolysiloxane, and polyethylene glycol. European Patent Application 117,360 to Cantrell et al., published Sep. 5, 1984, discloses compositions, containing a siloxane polymer having at least one nitrogen-hydrogen bond, a surfactant, and a solubilized titanate, zirconate or germanate, which act as both a conditioner and a hair styling aid.

European Patent Application 412,704 to Bolich et al., published Feb. 13, 1991, European Patent Application 408, 311 to Kawaguchi et al., published Jan. 16, 1991, and European Patent Application 412,707 to Torgerson et al., published Feb. 13, 1991, have suggested the use of silicone grafted acrylate copolymers in hair care application. U.S. Pat. No. 4,988,506 to Mitra et al., issued Jan. 29, 1991, describes the use of non-pressure sensitive polysiloxane-grafted copolymers in hair care compositions.

U.S. Pat. No. 5,061,481 to Suzuki et al., published Oct. 29, 1991, has disclosed the use of acryl-silicone graft copolymers in cosmetic compositions. These copolymers are prepared by the free radical polymerization of (meth) acrylate monomers with mono (meth)acrylate terminated polydiorganosiloxanes, thereby giving a copolymer which has a (meth)acrylate backbone with polydiorganosiloxane chain grafted to it. Polydiorganosiloxanes, being of high molecular weight, generally do not react completely. Thus the copolymers prepared by the above disclosed method contain ungrafted polydiorganosiloxane. Presence of free polydiorgano-siloxane and a silicone free polymer leads to either insolubility in desired solvents such as low boiling-point silicone oils such as polydimethylsiloxane with a low degree of polymerization, octamethylcyclo-tetrasiloxane ($D_4$), decamethylcyclopentasiloxane($D_5$), phenylpentamethyldisiloxane, and phenethylpentamethyl-disiloxane, and the like. Poor incorporation of silicone macromer into the copolymer also leads to adverse effects on the desired properties of cosmetics. In addition, silicone macromer, which is prepared by anionic polymerization of hexamethyltrisiloxane ($D_3$), is available only from limited number of sources and is an expensive commodity.

U.S. Pat. No. 5,032,460 to Kantner et al., published Jul. 16, 1991, assigned to the present assignee, has disclosed the preparation of vinyl-silicone copolymers which involve the use of a mercapto functional silicone compound as a chain transfer agent and their use as release coatings for various pressure sensitive adhesives. U.S. Pat. No. 4,987,180 to Saga et al., published Jan. 22, 1991, has disclosed the preparation of vinyl-silicone copolymers utilizing emulsion polymerization method and their use as fabric finishing agents. These copolymers comprise a silicone backbone with an acrylate chain grafted to it, i.e. the reverse molecular arrangement than that disclosed above in E.P. Applications 412,704; E.P. Application 408,311; E.P. Application 412, 707, and U.S. Pat. No. 5,061,481. The copolymers disclosed in U.S. Pat. No. 5,032,460 and 4,987,180 are prepared by the free radical polymerization of ethylenically unsaturated monomers with a mercapto functional silicone as a chain transfer agent. A number of references disclosed in U.S. Pat. No. 5,032,460 describe the preparation of mercapto functional silicone compounds.

SUMMARY OF THE INVENTION

A need exists for conveniently prepared and cost-effective polymers for use in cosmetic compositions. In the case of conventional makeup cosmetics, the composition should give a good sensation upon use, and should produce a cosmetic film that is sufficiently water resistant and friction resistant. In the case of personal care products for use in oral hygiene, the composition should provide a smooth, thin coating on teeth that prevents the adherence of bacteria to these surfaces. In the case of hair care compositions, the composition should provide excellent brilliance, gloss, conditioning and style retention to hair without stiff or sticky feel. In the case of moisturizers or other skin treatments, the composition should provide moisture-retaining properties by retarding evaporation of moisture through the skin, and should provide superior water and oil repellency and retentiveness of the makeup.

The present invention relates to cosmetics and personal care compositions containing a vinyl-silicone graft or block copolymer comprising a silicone polymer segment and a vinyl polymer segment. This block or graft copolymer is prepared by the free radical polymerization of a mercapto functional silicone chain transfer agent and vinyl monomers.

Compositions according to the present invention are effective moisture barriers and help retain the natural moisture of the skin. They also provide good sensation upon use, along with superior water-repellency, oil-resistance and good retentiveness of the makeup when used in cosmetics, such as foundation, lipsticks, rouges, and the like. In case of personal hygiene and personal care products, such as antiperspirants, deodorants, tooth paste, and the like, these polymers provide a smooth, water-resistant film which prevents the growth of bacteria. When used in hair care cosmetic formulations, these polymers provide excellent brilliance, gloss, conditioning, and style retention properties without a stiff and sticky feel.

BRIEF DESCRIPTION OF THE DRAWING

The FIGURE shows hair curl retention profiles over time in high humidity conditions.

DETAILED DESCRIPTION OF THE INVENTION

The copolymer used in the compositions of the present invention is either a graft or block copolymer and is represented by the following general formula.

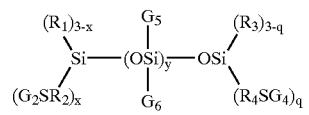

wherein $G_5$ represent monovalent moieties which can independently be the same or different selected from the group consisting of alkyl, aryl, alkaryl, alkoxy, alkylamino, fluoroalkyl, hydrogen, and —ZSA; A represents a vinyl polymeric segment consisting essentially of polymerized free radically polymerizable monomer, and Z is a divalent linking group. Useful divalent linking groups Z include but are not limited to the following: $C_1$ to $C_{10}$ alkylene, alkarylene, arylene, and alkoxyalkylene. Preferably, Z is selected from the group consisting of methylene and propylene for reasons of commercial availability.

$G_6$ represents monovalent moieties which can indpepedently be the same or different selected from the group consisting of alkyl, aryl, alkaryl, alkoxy, alkylamino, fluoroalkyl, hydrogen, and —ZSA;

$G_2$ comprises A;

$G_4$ comprises A;

$R_1$ represents monovalent moieties which can independently be the same or different and are selected from the group consisting of alkyl, aryl, alkaryl, alkoxy, alkylamino, fluoroalkyl, hydrogen, and hydroxyl; Preferably, $R_1$ represents monovalent moieties which can independently be the same or different selected from the group consisting of $C_{1-4}$ alkyl and hydroxyl for reasons of commercial availability. Most preferably, $R_1$ is methyl.

$R_2$ can independently be the same or different and represents divalent linking groups. Suitable divalent linking groups include but are not limited to the following: $C_1$ to $C_{10}$ alkylene, arylene, alkarylene, and alkoxyalkylene. Preferably, $R_2$ is selected from the group consisting of $C_{1-3}$ alkylene and $C_7$–$C_{10}$alkarylene due to ease of synthesis of the compound. Most preferably, $R_2$ is selected from the group consisting of —CH$_2$—, 1,3-propylene, and

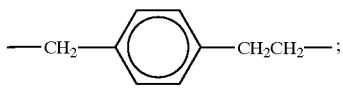

$R_3$ represents monovalent moieties which can independently be the same or different and are selected from the group consisting of alkyl, aryl, alkaryl, alkoxy, alkylamino, fluoroalkyl, hydrogen, and hydroxyl; Preferably, $R_3$ represents monovalent moieties which can independently be the same or different selected from the group consisting of $C_{1-4}$ alkyl and hydroxyl for reasons of commercial availability. Most preferably, $R_3$ is methyl.

$R_4$ can independently be the same or different and are divalent linking groups. Suitable divalent linking groups include but are not limited to the following: $C_1$ to $C_{10}$ alkylene, arylene, alkarylene and alkoxyalkylene. Preferably, $R_4$ is selected from the group consisting of $C_{1-3}$ alkylene and $C_7$–$C_{10}$alkarylene for reasons of ease of synthesis. Most preferably, $R_4$ is selected from the group consisting of —CH$_2$—, 1,3-propylene, and

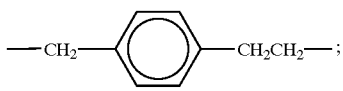

x is an integer of 0–3;

y is an integer of 5 or greater; preferably, y is an integer ranging from about 10 to about 270 in order to provide the silicone segment with a molecular weight ranging from about 750 to about 20,000. Most preferably, y is an integer ranging from about 40 to 15 about 270;

q is an integer of 0–3;

wherein at least one of the following is true:

q is an integer of at least 1;

x is an integer of at least 1;

$G_5$ comprises at least one —ZSA moiety;

$G_6$ comprises at least one —ZSA moiety.

As noted above, A is a vinyl polymeric segment formed from polymerized free radically polymerizable monomers. The selection of A is typically based upon the intended uses of the composition, and the properties the copolymer must possess in order to accomplish its intended purpose. If A comprises a block in the case of block copolymers, a polymer having AB and ABA architecture will be obtained depending upon whether a mercapto functional group —SH is attached to one or both terminal silicon atoms of the mercapto functional silicone compounds, respectively. The weight ratio of vinyl polymer block or segment, to silicone segment of the copolymer can vary. The preferred copolymers are those wherein the weight ratio of vinyl polymer segment to silicone segment ranges from about 98:2 to 40:60, in order that the copolymer possesses properties inherent to each of the different polymeric segment while retaining the overall polymer's solubility in low-viscosity silicone oil and/or low-boiling-point oil.

A Segment Monomeric Components

Representative examples of monomers that may be used to form the vinyl polymeric segment represented herein by A (hereafter "A monomers") are the lower to intermediate acrylic acid esters, or methacrylic acid esters of alkyl alcohols. Specific examples of such alcohols include methanol, ethanol, 1-propanol, 2-propanol, 1-butanol, 1,1-dimethyl ethanol, 2-methyl-1-propanol, 1-pentanol, 2-pentanol, 3-pentanol, 2-methyl-1-butanol, 3-methyl-1-butanol, 2-hexanol, 3-methyl-1-pentanol, 3-methyl-1-pentanol, cyclohexanol, 2-ethyl-1-butanol, 3-heptanol, benzyl alcohol, 2-octanol, 6-methyl-1-heptanol, 2-ethyl-1-hexanol, 3,5-dimethyl-1-hexanol, 3,5,5-trimethyl-1-hexanol, 1-decanol, and 1-dodecanol, and the like. Preferably, the alcohols have from 1 to 18 carbon atoms, and more preferably 1 to 12 carbon atoms, with the average number of carbon atoms being about 4 to 18. Some small amount of copolymerizable styrene, vinyl esters, vinyl chloride, vinylidine chloride, acrylonitrile, methacrylonitrile, acryloxypropyl tri-methoxysilane, methacryloxypropyl tri-methoxysilane, other acryloyl monomers and the like may be used. Such monomers are known in the art and many are commercially available. Particularly preferred monomers include isooctyl(meth)acrylate, isononyl (meth)acrylate, 2-ethylhexyl (meth)acrylate, lauryl (meth)acrylate, i-pentyl (meth)acrylate, n-butyl (meth)acrylate, i-butyl (meth)acrylate, methyl (meth)acrylate, ethyl (meth)acrylate, t-butyl(meth)acrylate, tridecyl (meth)acrylate, stearyl (meth)acrylate, and the like and mixtures thereof with above defined monomers.

Representative examples of polar monomers useful as A monomers include hydrophilic unsaturated monomers of a cationic, anionic, nonionic, or amphoteric nature which are polymerizable through radical polymerization. Examples of such polar monomers include acrylic acid, methacrylic acid, itaconic acid, vinyl acetic acid, acrylonitrile, fumaric acid, maleic acid, maleic anhydride, crotonic acid, acrylamide, vinyl pyridine, vinyl pyrrolidone, N,N-dimethylacrylamide, N-t-butylacrylamide, methacrylonitrile, or salts thereof and the like.

A monomers can also be half esters of an unsaturated polybasic acid anhydride such as succinic anhydride, phthalic anhydride, 4-methacryloxyethyl-trimellitic anhydride (4-META) or the like with hydroxyl groups containing (meth)acrylates such as hydroxy ethyl (meth)acrylate, hydroxy propyl (meth)acrylate or the like. In addition, polymeric monomers or macromonomers, as defined hereinafter, are also useful as monomers. Representative examples of such polymeric monomers are poly(styrene), poly(α-methyl styrene), poly(vinyl toluene), polymethyl (meth)acrylate, and poly(oxyalkylene) macromonomers.

Preferred representative examples also include highly polar acrylic and methacrylic monomers. A highly polar monomer as defined herein are acrylic or methacrylic monomers having at least one highly polarizing group such as hydroxyl (OH), alkoxy, amino (primary, secondary, and tertiary), ionic groups (e.g., quaternary ammonium, carboxylate salt, sulfonic acid salt, etc.), and alkenyl heterocycles.

In the case of hydroxyl-containing monomers, such monomers may be more specifically represented by the general formula:

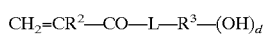

CH$_2$=CR$^2$—CO—L—R$^3$—(OH)$_d$ where R$^2$=H, methyl, ethyl, cyano or carboxymethyl, L=—O, —NH, d=1–3 and R$^3$ is a hydrocarbyl radical of valence d+1 containing from 1 to 12 carbon atoms. The preferred monomers in this class are hydroxyethyl (meth)acrylate, hydroxypropyl (meth)acrylate, hydroxybutyl (meth)acrylate, glycerol mono(meth)acrylate, tris (hydroxymethyl) ethane monoacrylate, pentaerythritol mono(meth)acrylate. N-hydroxymethyl (meth)acrylamide, hydroxyethyl (meth)acrylamide and hydroxypropyl (meth) acrylamide.

The highly polar monomers may also be alkoxy substituted (meth)acrylates or (meth)acrylamides such as methoxyethyl (meth)acrylate, 2(2-ethoxyethoxy)ethyl (meth) acrylate, polyethylene glycol mono(meth)acrylate or polypropylene glycol mono(meth)acrylate.

Amino groups containing highly polar monomers may be represented by the general formula:

CH$_2$=CR$^2$—CO—L—R$^3$—(NR$^4$R$^5$)$_d$ where R$^2$, L, R$^3$, and d are as defined above and R$^4$ and R$^5$ are H or alkyl groups of 1 to 12 carbon atoms or together they constitute a carbocyclic or heterocyclic group. Preferred monomers of this class are aminoethyl (meth) acrylate, aminopropyl (meth)acrylate, N,N-dimethylaminoethyl (meth)acrylate, N,N-diethylaminoethyl (meth)acrylate, N,N-dimethylaminopropyl (meth) acrylamide, N-isopropylaminopropyl (meth)acrylamide, and 4-methyl-1-acryloyl-piperazine.

Monomers that have substituted or unsubstituted ammonium groups may be represented by the general formula:

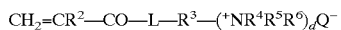

CH$_2$=CR$^2$—CO—L—R$^3$—($^+$NR$^4$R$^5$R$^6$)$_d$Q$^-$ where R$^2$, R$^3$, R$^4$, R$^5$, L, and d are as defined above, and where R$^6$ is H or alkyl group of 1–12 carbon atoms and Q$^-$ is an organic or inorganic anion. Preferred examples of such monomers are 2-N,N,N-trimethylammoniumethyl (meth) acrylate, 2-N,N,N-triethylammonium ethyl (meth)acrylate, 3-N,N,N-triethylammonium propyl (meth)acrylate, N(2-N', N',N'-trimethylammonium) ethyl (meth)acrylamide, N-(dimethylhydroxyethylammonium) propyl (meth) acrylamide and the like, where the counterion may be chloride, bromide, acetate, propionate, laurate, palmitate, stearate etc., or the modified products with propane sultone of the aforementioned amine derivatives of (meth)acrylic acid or (meth)acrylamide. The monomers can also be N,N-dimethyldiallyl ammonium salt of an organic or inorganic counterion.

Ammonium group containing polymers can also be prepared by acidifying the amino group of the polymer with organic or inorganic acid to a pH where the pendant amino groups are substantially protonated. Totally substituted ammonium group containing polymers may be prepared by alkylating the above described amino polymers with alkylating groups, the method being commonly known in the art as the Menschutkin reaction.

The highly polar A monomers can also be sulphonic acid group containing monomers e.g. vinyl sulphonic acid, styrene sulphonic acid, 2-acrylamido-2-methyl propane sulphonic acid, allyloxybenzene sulphonic acid and the like. These monomers may be used in the protonated acid form as monomers, with the corresponding polymers neutralized with an organic or inorganic base to give the salt form of the polymers.

The highly polar monomers can be other alkenyl heterocycles such as vinyl pyridines; vinyl imidazoles, vinyl benzimidazoles; 2-ethenyl-4,4-dimethyl-1,3-oxazoline-5-one (vinyl azlactone); N-vinyl pyrrolidone (NVP); vinyl furans and the like. These heterocyclic comonomers provide sites for hydrogen bonding with polar substrates and improve adhesion of the resultant polymers to such substrates.

The polymers for use in the compositions of the present invention are prepared by polymerizing the free radically polymerizable monomers using a mercapto functional silicone chain transfer agent. The terms "mercapto functional silicone compounds", "mercapto functional silicone chain transfer agent", and "mercapto functional silicone macromolecular chain transfer agent" are used interchangeably throughout. The reaction comprises free radical polymerization of mercapto functional silicone with vinyl monomers.

Mercapto Functional Silicone Chain Transfer Agents

The formula of the mercapto functional silicone macromolecular chain transfer agent useful in the preparation of vinyl-siloxane copolymer is set forth below.

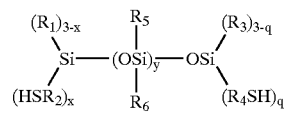

wherein all moieties are as defined above and wherein R$_5$ are monovalent moieties which can be the same or different and are selected from the group consisting of alkyl, aryl, alkaryl, alkoxy, alkylamino, hydroxyl, fluoroalkyl, hydrogen, and —ZSH wherein Z is a divalent linking group. Useful divalent linking groups Z include but are not limited to the following: C$_1$ to C$_{10}$ alkylene, alkarylene, arylene, and alkoxyalkylene. Preferably, Z is selected from the group consisting of methylene and propylene.

When R$_5$ does not comprise a —ZSH group, R$_5$ is preferably selected from the group consisting of C$_{1-3}$ alkyl or fluoroalkyl, and phenyl. Most preferably, R$_5$ comprises a methyl group.

R$_6$ are monovalent moieties which can be the same or different and are selected from the group consisting of alkyl, aryl, alkaryl, alkoxy, alkylamino, hydroxyl, fluoroalkyl, hydrogen, and —ZSH, wherein Z is a divalent linking group as defined above.

When R$_6$ does not comprise a —ZSH group, R$_6$ is preferably selected from the group consisting of C$_{1-3}$ alkyl or fluoroalkyl, and phenyl. When R$_6$ does not comprise a —ZSH group, R$_6$ most preferably comprises a methyl group.

In the structure illustrated above, y is an integer of 5 or greater. Preferably, y is an integer ranging from about 10 to about 270 x and q are integers of 0 to 3, wherein at least one of the following is true:

q is an integer of at least one; x is an integer of at least one; $R_5$ comprises at least one —ZSH moiety; or $R_6$ comprises at least one —ZSH moiety.

The number of mercapto functional groups on the mercapto functional silicone compound can vary. If the number of mercapto functional groups on the mercapto functional silicone compound is too high, desired properties such as desirable sensational feeling in makeup cosmetics, and soft feel in hair care cosmetics will be lost. If the number of mercapto functional groups on the mercapto functional silicone compound is too low, desired properties such as style retention properties in hair care compositions may not be obtained. The SH equivalent weight of the mercapto functional silicone compound preferably is between 400–4000, and more preferably 1000–2000.

The mercapto functional silicone compounds useful in the method of the present invention can be prepared by any known method including, for example, (1) cohydrolysis-condensation of a mixture consisting of an organoalkoxysilane having one or more mercapto-substituted hydrocarbon groups and an alkoxysilane possessing no mercapto group, (2) reaction of an organoalkoxysilane having one or more mercapto-substituted hydrocarbon groups with a cyclic organopolysiloxane or with a silanol terminated diorganopolysiloxane possessing no mercapto groups, (3) an equilibration reaction of a cyclic or linear chain organopolysiloxane having one or more mercapto substituted hydrocarbon groups with a cyclic or linear chain organopolysiloxane having no mercapto groups, (4) reaction of an organopolysiloxane having one or more nucleophilic groups such as an aminoalkyl with an electrophilic reagent such as 3-mercaptopropionic acid in order to yield a mercapto-derivatized organopolysiloxane, and (5) reaction of an organopolysiloxane having one or more electrophilic groups such as haloalkyl with a nucleophilic reagent such as an alkali metal sulfide to yield a mercapto-derivatized organopolysiloxane.

U.S. Pat. No. 4,238,393; U.S. Pat. No. 4,046,795; U.S. Pat. No. 4,783,490; U.S. Pat. No. 5,032,460 and Canadian Patent 1,233,290 describe the preparation of mercapto functional silicone compounds.

In order to form a graft vinyl-silicone copolymer, at least one mercapto functional group of the mercapto functional silicone compound must be bonded to a silicon atom within the silicone segment. Thus, at least one $R_5$ group or one $R_6$ group of the mercapto functional silicone compound must comprise —ZSH in order to form a vinyl-silicone graft copolymer, regardless of the existence of any mercapto functional group bonded to the terminal silicon atom.

Polymerizable Silanes

The polymerizable silanes are acryloxyalkyl-alkoxysilanes having a general formula of $D(G)SiR_a(Q)_{3-a}$, wherein symbol D represents the group CH2=C (R') —COO—. The symbol R which may be the same or different, represents methyl, ethyl, n-propyl, vinyl or phenyl group. The symbol R' represents a hydrogen atom or a methyl group, the symbol Q, which may be the same or different, represent methoxy, ethoxy, n-propoxy or β-methoxyethoxy groups, and any two of the symbols Q taken together can represent a group of the formula:

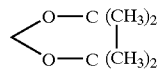

The symbol G represents a linear or branched chain alkylene having 1 to 8 carbon atoms, and the symbol a represents a value of zero to two. Representative examples of silanes are:

$CH_2$=CH COO $CH_2$ Si $(CH_3)_2(OCH_3)$
$CH_2$=CH COO $CH_2$ Si $CH_3(OCH_3)_2$
$CH_2$=CH COO $(CH_2)_3Si(CH_3)_2$ $(OC_2H_5)$
$CH_2$=CH COO $(CH_2)_3Si$ $(OC_2H_5)_3$
$CH_2$=CH COO $(CH_2)_3Si$ $(OCH_3)_3$
$CH_2$=CH COO $(CH_2)_4Si$ $(OCH_2CH_2OCH_3)_3$
$CH_2$=CH COO $(CH_2)_3Si$ $(O-nC_3H_7)_3$
$CH_2$=C(Me) COO $CH_2Si-CH_3$ $(OCH_3)_2$
$CH_2$=C(Me) COO $(CH_2)_3Si$ $(OCH_3)_3$
$CH_2$=C(Me) COO $(CH_2)_3Si$ $(OC_2H_5)_3$
$CH_2$=C(Me) COO $(CH_2)_3Si$ $(OCH_2CH_2OCH_3)_3$
$CH_2$=C(Me) COO $(CH_2)_4$ $Si-(C_6H_5)$ $(OCH_3)_2$
$CH_2$=C(Me) COO $(CH_2)_4CH$ $(C_2H_5)CH_2Si-(C_2H_5)$ $(OCH_3)_2$

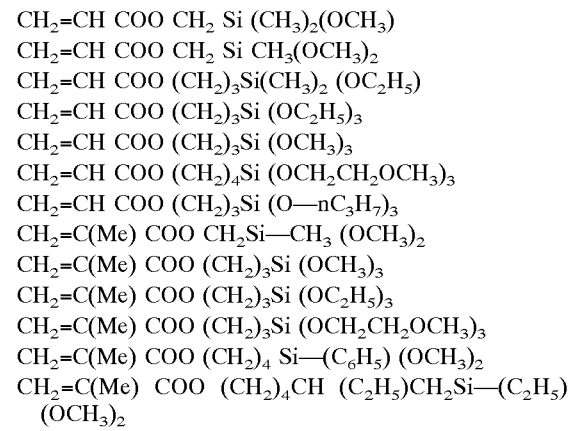

These silanes may be prepared by reaction of intermediates of the formula Cl—G—$SiR_a(Q)_{3-a}$, with an organic acid of the formula $CH_2$=C(R') COOH. The reaction is advantageously conducted in an organic aprotic solvent such as N-methylpyrrolidone-2, N,N-dimethylformamide, and in the presence of an HCl acceptor such as triethylamine. In place of the organic acids, their alkali metal salts may be used. In this case, it is unnecessary to utilize an HCl acceptor in the reaction mixture. The silanes are readily available on the silicone market. These silanes when desired can be used in 0.01% to 20% and preferably from 0.05% to 10% during polymerization.

Methods of Initiation

The homolytic decomposition of the initiator to form free radicals can be induced by heat energy (thermolysis), light energy (photolysis), or the addition of a suitable catalyst. "Initiator free" polymerization may also be induced electronically or by exposure to ionizing radiation.

The decomposition rate of the initiator during thermolysis depends on the chemical nature of the initiator, the reaction temperature, and the solvent (if any) used.

The decomposition rate of the initiator during photolysis depends mainly on the chemical nature of the initiator and the intensity and wavelength of the radiation.

Light energy can be supplied to induce the homolytic decomposition of the initiator by means of visible or ultraviolet sources including low intensity fluorescent black light lamps, medium pressure mercury arc lamps, and germicidal mercury lamps.

The selection of a preferred light energy source will depend on the chosen photoinitiator.

The decomposition of the initiator can also be accomplished by using a suitable catalyst. Catalyst induced initiator decomposition involves an electron transfer mechanism resulting in a reduction-oxidation (redox) reaction. Initiators such as peroxides and hydroperoxides are more susceptible to this kind of decomposition.

Catalysts useful in inducing the homolytic decomposition of the initiator include but are not limited to the following: amines and metal ions used in combination with peroxide or hydroperoxide initiators, and bisulphite or mercapto compounds used in combination with persulphate initiators.

The preferred method of initiation comprises thermolysis which can be readily used in standard reactors. Thermolysis also provides ease of control of the reaction rate and exotherm.

Initiators

Useful initiators in the polymerization method of the present invention are well known to practitioners skilled in the art and are detailed in chapters 20 & 21, Macromolecules, vol 2, 2nd Ed., H. G. Elias, Plenum Press, 1984, New York. Useful thermal initiators for use in the method of the present invention include, but are not limited to the following: azo compounds such as 2,2'-azobis-(isobutyronitrile), dimethyl-2,2'-azo-bis-isobutyrate, azo-bis-(diphenyl methane), 4,4'-azo-bis-(4-cyanopentanoic acid); peroxides such as benzoyl peroxide, cumyl peroxide, tert-butyl peroxide, cyclohexanone peroxide, glutaric acid peroxide, lauroyl peroxide, methyl ethyl ketone peroxide; hydrogen peroxide, hydroperoxides such as tert-butyl hydroperoxide, and cumene hydroperoxide; peracids such as peracetic acid and perbenzoic acid, potassium persulfate; and peresters such as diisopropyl percarbonate.

Certain of these initiators (in particular the peroxides, hydroperoxides, peracids, and peresters) can be induced to decompose by addition of a suitable catalyst rather than thermally. This redox method of initiation is described in Elias, Chapter 20.

Useful photochemical initiators include but are not limited to benzoin ethers such as diethoxyacetophenone, oximino-ketones, acylphosphine oxides, diaryl ketones such as benzophenone, and 2-isopropyl thioxanthone, benzil and quinone derivatives, and 3-ketocumarines as described by S. P. Pappas, J. Rad. Cur., July 1987, p. 6.

Preferably, the initiator used comprise a thermally decomposed azo or peroxide compound for reasons of solubility and control of the reaction rate. Most preferably, the initiator used comprises 2,2'-azobis(isobutyronitrile) for reasons of cost and appropriate decomposition temperature.

Solvents

The use of a solvent is optional in the present polymerization method. Preferably, a solvent is utilized for reasons of decreasing the viscosity during the reaction to allow for efficient stirring and heat transfer. The organic solvent used in the free radical polymerization can be any organic liquid which is inert to the reactants and which will not otherwise adversely affect the reaction.

Suitable solvents include but are not limited to esters such as ethyl acetate and butyl acetate; ketones such as methyl ethyl ketone, methyl isobutyl ketone, methyl propyl ketone, and acetone; alcohols such as methanol, ethanol, isopropanol, and butanol; and mixtures of two or more of the above mentioned solvents.

Other solvent systems are useful as well. Aliphatic and aromatic hydrocarbons can very well be used though some time they lead to the precipitation of the vinyl polymeric segment from solution, resulting in a non-aqueous dispersion polymerization. Such hydrocarbon solvents become more useful when admixed with other polar solvents providing a good control on molecular weight of the final polymer.

Low-viscosity silicone oil with linear, cyclic, or branched structure having a boiling point below 260° C., at normal pressure, and a viscosity below 100 cSt, such as polydimethylpolysiloxane with a low degree of polymerization, octamethylcyclotetra-siloxane($D_4$), decamethylpentacyclotetrasiloxane($D5$), phenylpentamethyldisiloxane, hexamethyldisiloxane, phenethylpentamethyl disiloxane, and the like, can very well be used. Hexamethylcyclotrisiloxane($D_3$) can be present in small amount in the above mixtures, but is generally not usable to solubilize the copolymers as it is solid at room temperature.

The solvent, if utilized in the free radical polymerization, may be any substance which is liquid in a temperature range of about −10° C. to about 50° C., does not interfere with the energy source or catalyst used to dissociate the initiator to form free radicals, is inert to the reactants and product and will not otherwise adversely affect the reaction. The amount of solvent, if used, is generally about 30 to 95 percent by weight based on the total weight of the reactants and solvent. Preferably, the amount of solvent utilized ranges from about 40 to about 65 percent by weight based upon the total weight of the reactants and solvent for reasons of yielding fast reaction times and high molecular weight of the polymer at appropriate product viscosities.

If the polymerization is conducted in the absence of a solvent, the free-radically polymerizable mixture of vinyl monomer, and mercapto functional silicone should remain homogeneous during the course of the reaction, allowing for the desired reaction between the mercapto functional silicone, initiator, and monomers.

Method of Polymerization

The free radically polymerizable monomers, the initiator, the mercapto functional silicone compound and any solvent employed are charged into an appropriate vessel. But, alternatively, if desired, these monomers can also be used in such a way that some of them in types and/or amounts are added to the polymerization reaction separately. If photolysis is conducted to decompose the initiator, the reactants and any solvent employed are charged into an energy source-transparent vessel and therein subjected to the energy source. If the energy source is ultraviolet light radiation, a suitable ultraviolet light-transparent vessel is utilized.

If thermolysis is used to decompose the initiator, the reactants and any solvent employed are charged into a suitable glass or metal reactor, and therein subjected to the thermal energy source. If catalysis is used to decompose the initiator, a glass or metal reactor can also be utilized.

The reaction is preferably conducted in a vessel with agitation to permit uniform exposure of the reactants to the energy source. While most of the reactions have been conducted by employing a batch process, it is possible to utilize the same technology in a continuous polymerization operation.

Reaction times on the order of 1 to 40 hours have been found typical, depending upon the amount and type of solvent used, the amount and type of initiator used, temperatures or photolytic energy supplied, and the nature of the free radically polymerizable monomers.

The block or graft copolymers when necessary or desirable can be blended with a compatible modifier in order to optimize physical properties. The use of such modifiers is common in the art. For example, it may be desirable to include such materials as pigments, fillers, stabilizers, or various polymeric additives.

The vinyl-silicone copolymers can be recovered by standard procedures such as evaporation of solvent, precipitation after polymerization into a suitable organic solvent such as methanol, hexane and the like. Standard extraction techniques can also be used if desired. Polymer can also be taken into a different solvent either a solvent exchange process, e.g., by adding a higher boiling solvent and then distilling out the low boiling solvent or by azeotropic distillation, a technique well known in the art.

Waterborne coatings can also be prepared by following the method disclosed in U.S. Pat. No. 5,032,460 to Kantner et al.

Vinyl-silicone copolymers suitable for waterborne applications are either those containing ionic functionalities in the vinyl polymeric block or segment or those containing acidic or basic functionalities which on neutralization yield ionic functionalities. Certain of these polymers can be modified to obtain a water dispersible formulation by a neutralization technique, specifically those copolymers containing acidic or basic functionality in the vinyl segment.

Copolymers containing acidic functionality are obtained by copolymerizing acidic monomers into the vinyl block or segment. Suitable acidic monomers include those containing carboxylic acid functionality such as acrylic acid, methacrylic acid, itaconic acid, and the like; those containing sulfonic acid functionality such as 2-sulfoethyl methacrylate; and those containing phosphonic acid functionality.

Copolymers containing basic functionality are obtained by copolymerizing basic monomers into the vinyl block or segment. Suitable basic monomers include those containing amine functionality such as vinyl pyridine, N,N-diethylaminoethyl methacrylate, N,N-dimethylamino-ethyl methacrylate, N,N-diethylaminoethyl acrylate, N,N-dimethylaminoethyl acrylate, and N-t-butylaminoethyl methacrylate.

Preferred acidic monomers include acrylic acid and methacrylic acid. Preferred basic monomers include N,N-dimethylaminoethyl methacrylate, and N,N-dimethylaminoethyl acrylate.

In order to achieve water compatibility or dispersibility, a certain minimum ionic content in the copolymer is required. The exact amount varies with the particular polymer formulation, the molecular weight of the polymerized silicone segment, and other features of the individual copolymer. Generally a minimum of about 2% by weight of ionic content will yield a stable dispersion, considering the weight of the ionic group to include only the simplest of constructions, e.g., the monomer from which the ionic group is derived plus the base or acid used to neutralize it, as the molecular weight of the ion. Preferred copolymers incorporate above about 4% ionic content.

It has surprisingly been found that polymers according to the present invention that are the reaction product of specific selected monomer components provide particular benefits for hair care applications. These preferred polymers are the reaction product of a) 5–40 weight percent of a mercapto-functional silicone compound of the formula

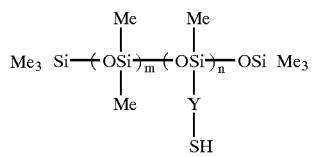

wherein the mole ratio of m/n is 9–49,
Y is selected from C1–10 alkylene and alkarylene having at least 10 carbons, wherein the bracketed groups may be randomly distributed throughout the compound, said compound having a total number average molecular weight of 350–20,000;
b) 0–25 weight percent of a soft monomer; and
c) 35–95 weight percent of a hard monomer;
wherein the glass transition temperature of the vinyl portion of the polymer is about 60–110° C.

In the case of compositions where delivery of polymer directly from a water dispersion is desired, the polymers may contain polar functionality in an amount sufficient to render the polymer dispersible in water. The preferred mode of providing such polymer functionality is to select an acid-containing soft or hard monomer, which acid may be neutralized as discussed above to provide an ionic species.

A more preferred glass transition temperature of the vinyl portion of the polymer is about 80–100° C.

In the case of hair-care compositions, this combination of hydrophobic silicone-containing group with the vinyl "tail" having a selected glass transition temperature provides the desired adhesion to the intended substrate and low surface energy without being stiff. Surprisingly, this preferred range of polymers may even contain substantial hydrophilic components without having a negative effect on hair style, even in humid conditions.

The glass transition temperature of the polymer is determined experimentally using Differential Scanning Calorimetry using the following technique. One gram of polymer is dissolved in 1.5 grams of an appropriate organic solvent, cast into a 70 mm diameter aluminum dish and dried in an air forced oven at 105° C. for 30 minutes. A small amount of the resulting sample is placed in the DSC chamber of a Perkin-Elmer DSC-2 differential scanning calorimeter under $N_2$ atmosphere. The sample was cooled from room temperature to −150° C. with liquid $N_2$ and then heated to 150° C. at 20° C. per minute. The Tg was taken as the midpoint of the curve in the glass transition range.

Two glass transition temperatures are observed in testing the preferred polymers. The first low $T_g$ corresponds to the silicone portion of the polymer. The second higher $T_g$ corresponds to the vinyl portion of the polymer.

The number average molecular weight was determined by gel permeation chromatography (GPC), using a polystyrene standard.

While not being bound by theory, it is believed that the selection of the glass transition temperature, together with the chemical properties of the various components as set forth herein, provides a unique combination of properties that allow for good adhesion to the hair together with style retention, at the same time having hair that feels soft and not stiff to the touch. The preferred polymers have a selected $T_g$ that allows the polymer to adhere to the hair, perhaps with the assistance of a plasticization effect by the solvent used to deliver the polymer to the hair. As the carrier solvent dissipates, the $T_g$ of the polymer is no longer modified by a solvent effect, and is sufficiently high to achieve good style hold. Remarkably, the hair style is retained without a stiffness being imparted to the hair. If the glass transition temperature of the vinyl portion of the polymer is selected to be lower than the identified range, the style retention is not as good. If the glass transition temperature is too high, the hair will feel brittle and stiff.

The mercapto-functional silicone compound preferably has a number average molecular weight of 4,000–15,000, and more preferably of 8,000–12,000. Mercapto-functional silicone compounds wherein Y is C2-5 alkyl, and more particularly C3 are preferred. A more preferred mole ratio of m/n is 15–25.

A "soft" monomer is defined as a monomer wherein the corresponding homopolymer has a $T_g$ of less than about 20° C. Typically, the soft monomer provides flexibility, elongation and adhesiveness in the copolymer.

The soft monomer is typically a monomeric acrylic or methacrylic acid ester of an alkyl alcohol containing a single hydroxyl, the alcohol being further described as having from one to about 14 carbon atoms when the soft monomer is an acrylic acid ester, and about 7 to 18 carbon atoms when the soft monomer is a methacrylic acid ester.

Examples of suitable acrylic acid esters for use as the soft monomer include the esters of acrylic acid with alcohols such as methanol, ethanol, 1-propanol, 2-propanol, 2-methyl-1-propanol, 1-butanol, 2-butanol, 1-pentanol, 2-pentanol, 3-pentanol, 2-methyl-1-butanol, 1-hexanol, 2-hexanol, 2-methyl-1-pentanol, 3-methyl-1-pentanol, 2-ethyl-1 butanol, 3,5,5-trimethyl-1-hexanol, 3-heptanol, 1-octanol, 2-octanol, iso-octyl alcohol, 2-ethyl-1-hexanol, 1-decanol, 1-dodecanol, 1-tridecanol, 1-tetradecanol, and the like.

Examples of suitable methacrylic acid esters for use as the soft monomer include the esters of methacrylic acid with alcohols such as 3-heptanol, 1-octanol, 2-octanol, iso-octyl alcohol, 2-ethyl-1-hexanol, 1-decanol, 1-dodecanol, 1-tridecanol, 1-tetradecanol, 1-octadecanol and the like.

Other examples of soft monomers that can be used are vinyl monomers having the requisite $T_g$ values including dienes, such as butadiene and isoprene; acrylamides, such as N-octylacrylamide; vinyl ethers, such as butoxyethylene, propoxyethylene and octyloxyethylene; vinyl halides, such as 1,1-dichloroethylene; and vinyl esters such as vinyl versatate, vinyl caprate and vinyl laurate.

The preferred soft monomer is selected from the group consisting of methyl acrylate and ethyl acrylate.

It is to be understood that the copolymer may comprise a single type of soft monomer or may comprise two or more different soft monomers.

A "hard" monomer is defined as a monomer wherein the corresponding homopolymer has a $T_g$ of more than about 20° C., and preferably more than about 40° C. Typically, the hard monomer is a monomer that provides tensile strength and also reduces tack in the copolymer.

The hard monomer is typically acrylic acid, methacrylic acid and/or a monomeric methacrylic acid ester of an alkyl alcohol containing a single hydroxyl. The alcohol contains from 1 to about 6 carbon atoms, and preferably 1 to about 4 carbon atoms.

Examples of suitable monomers for use as the hard monomer include the esters of methacrylic acid with alcohols such as methanol, ethanol, 1-propanol, 2-propanol, 1,1-dimethyl ethanol, 1-butanol, 2-butanol, 1-pentanol, 2-pentanol and 3-pentanol.

Other examples of hard monomers are monomers having the requisite $T_g$ values include methacrylates having a structure other than delineated above, such as benzyl methacrylate, cyclohexyl methacrylate and isobornyl methacrylate; methacrylamides, such as N-t-butylmethacrylamide; acrylates, such as t-butyl acrylate and isobornyl acrylate; acrylamides, such as N-butylacrylamide and N-t-butylacrylamide; diesters of unsaturated dicarboxylic acids such as diethyl itaconate and diethyl fumarate; vinyl nitriles, such as acrylonitrile, and methacrylonitrile; vinyl esters, such as vinyl acetate and vinyl propionate; and monomers containing an aromatic ring such as styrene; α-methyl styrene and vinyl toluene.

The preferred hard monomer is selected from the group consisting of methyl methacrylate, ethyl methacrylate, isobutyl methacrylate and isobornyl methacrylate.

It is to be understood that the copolymer may comprise a single type of hard monomer or may comprise two or more different hard monomers.

Hair care compositions containing a polymer as preferred but not containing a functionality in an amount sufficient to render the polymer dispersible in water may be readily delivered to the hair in emulsion form, wherein the oil phase of the emulsion is preferably selected from a low boiling solvent that will quickly dissipate upon application to the hair. Preferred oils include low-viscosity silicone oil with linear, cyclic, or branched structure having a boiling point below 260° C., at normal pressure, and a viscosity below 100 cSt, such as polydimethylpolysiloxane with a low degree of polymerization, octamethylcyclotetra-siloxane ($D_4$), decamethylpentacyclotetrasiloxane($D5$), phenylpentamethyldisiloxane, hexamethyldisiloxane, phenethylpentamethyl disiloxane, and the like.

The vinyl-silicone copolymers as described herein, in addition to skin care products, such as cosmetics, can also be used in a variety of applications such as ink receptors, thermoplastics, mold release agents, mildew preventives, moth resisting agents, corrosion resistant materials, softeners, permselective membranes, fabric protectors, textile treatment, additives to paints and varnishes such as wall paints, automotive paints and the like, marine anti-fouling agents, and metal coatings and the like. In accordance with the present invention, these copolymers can be utilized to formulate various other type of cleaning products which are not directly used on skin. Examples of such products are cleaning products for shower area such as hard surface cleaner, laundry products, dish washing products, and the like to impart a smooth, silky, and water repellent properties on such surfaces.

Cosmetic Compositions Containing Vinyl-Silicone Copolymers

Low-viscosity silicone oil can be incorporated into the copolymer to provide a stable gel composition. There are no specific limitations as to the type of a low-viscosity silicone oil for use. Any silicone oil having a viscosity below 100 cSt, preferably of 2–20 cSt, can suitably be used. The use of a large amount of a higher viscosity silicone oil may decrease the mutual solubility of the silicone oil and vinyl-silicone copolymer. This results in an oily sensation and tends to impair the feeling upon use of the resulting product. Examples of low-viscosity silicone oils include low-polymerization-degree polydimethylsiloxanes, polymethylphenylsiloxane, and the like. If necessary, two or more of low-viscosity silicone oils can be used in combination. Silicone oil of the type mentioned above can be used as a low-viscosity silicone oil either independently or in combination. A desirable range to be incorporated is 30–94.8% by weight.

A gel composition of the present invention usable in cosmetics, personal hygiene, and personal care products can be prepared by blending vinyl-silicone copolymer and a low-viscosity silicone oil and heating the mixture to dissolution; or by dissolving copolymer into a volatile organic solvent, and adding a low-viscosity silicone oil to the solution, followed by removal of the volatile organic solvent; or by carrying out the polymerization in low-viscosity silicone oils. The ratio of vinyl-silicone copolymer to low-viscosity silicone oil varies depending on the type of copolymer. Normally, the ratio by weight of vinyl-silicone copolymer to low-viscosity silicone oil is 5:95 to 70:30, with a preferable range being 10:80 to 40:60. If the amount of the low-viscosity silicone oil is too large in proportion to copolymer, the resulting gel composition becomes fluid so that a gel composition having acceptable solidity can not be obtained. If the amount of the copolymer is too large, on the other hand, a soft flexible solid gel composition cannot be obtained.

In the present invention, a solid gel composition having varied solidity, ranging from a comparatively hard gel to a comparatively soft gel, can be produced by changing the proportion of copolymer and a low-viscosity silicone oil, or the vinyl chain length, silicone chain length and/or amount of silicone in the copolymer. If the proportion of the vinyl-silicone copolymer is increased or a larger amount of methylmethacrylate is introduced into the vinyl chains of the copolymer, a solid gel giving suitable solidity to touch is obtained. On the other hand, a soft, flexible gel composition can be produced by introducing a large amount of butylacrylate, or 2-ethylhexyacrylate into the vinyl chains of the copolymer.

The solid gel composition thus prepared gives a soft, stable, smooth, and fresh sensation upon use. By using the solid gel composition as a component, very useful cosmetic compositions in which the excellent characteristics of the solid gel are fully exhibited can be produced. Such cosmetics include basic cosmetics for use with the face, hands, and feet such as creams, emulsions, and the like; hair cosmetics such as hair treatment agents, and the like; makeup cosmetics such as foundations, rouges, face powders, lipsticks, eyeliners, eyeshadows, mascaras, and the like; protective cosmetics such as insect repellent cream, sunscreen lotion/cream, and the like; and personal care/personal hygiene products such as toothpaste, deodorants, antiperspirant, and the like. The kind of cosmetics to which the gel composition of the present invention is applied are by no means limited to those given here.

The amount of the solid gel to be incorporated into a cosmetic composition can be determined depending on the use to which the cosmetic composition is directed within a range of 1–100% by weight. The use of the solid gel alone may achieve the purpose of the present invention.

The gel composition may comprise a small amount of partially crosslinked vinyl-silicone copolymer or partially crosslinked organopolysiloxane polymeric compound. When incorporated in cosmetic compositions, these polymers provide a smooth and fresh feel upon use. A gel composition comprising 5–60% by weight of a vinyl-silicone copolymer, 30–94.8% by weight of a low-viscosity silicone oil, and 0.2–40% by weight of a partially crosslinked organopolysiloxane is particularly useful for incorporating in a cosmetic composition. The amount of 5–60% by weight of vinyl-silicone copolymer is preferable, because the intended effect can not be produced if the amount is less than 5% by weight, and the cosmetic composition becomes too hard at an amount exceeding 60% by weight. If and when desired, partially crosslinked organopolysiloxane polymeric compound can be incorporated in the gel composition by simply blending the vinyl-silicone copolymer, the low-viscosity silicone oil, and partially crosslinked organopolysiloxane polymeric compound. An alternative method is to prepare a gel composition from the vinyl-silicone copolymer and the low viscosity silicone oil, and a gel composition from the partially crosslinked organopolysiloxane polymeric compound and the low-viscosity silicone oil, followed by blending the two gel compositions. This latter method can produce a gel composition having different characteristics from that produced by blending the three components at the same time. Specifically, such a gel composition can contain a greater amount of silicone oil in a more stable manner. This provides the resulting cosmetic composition with superior smoothness and freshness as well as even better stability over time. This gel composition can be incorporated in an amount of 2–100% by weight based on the total weight of the cosmetics and personal care composition.

Vinyl-silicone copolymers have excellent film-forming capability. Thus, the cosmetic and personal care compositions to which these copolymers are incorporated can produce a film exhibiting a superior water-resistance, oil-resistance, and other characteristics required for cosmetic films. A cosmetic composition for application to nails, such as a nail enamel, composition can be prepared by dissolving the vinyl-silicone copolymer into a low-boiling-point oil or a volatile solvent. The cosmetic composition thus prepared can produce a continuous film immediately upon application. The low-boiling-point oil used here includes volatile hydrocarbon oils having a boiling point below 260° C., at normal pressure. There are no special limitations as to the types of hydrocarbons. Any types usually used for cosmetics can be used. Examples of a volatile solvent include ethyl acetate, butyl acetate, acetone, toluene, ethyl alcohol, i-propyl alcohol, n-propyl alcohol, 1,2-propylene glycol, 1-methoxy-2-propanol, and the like. Another type of low boiling-point oil is a volatile, linear, cyclic, or branched silicone oil having a boiling point below 260° C., at normal pressure and a viscosity below 10 cSt, such as polydimethylsiloxane with a low degree of polymerization, octamethylcyclotetrasiloxane(D4), decamethylcyclopentasiloxane(D5), phenylpentamethyldisiloxane, hexamethyldisiloxane, phenethylpentamethyldisiloxane, and the like. The amount of vinyl-silicone copolymer to be incorporated into the cosmetic composition is usually 0.03–70% by weight, and preferably. 0.2 to 30%. If the amount of the copolymer is too small, the film produced by the cosmetic composition becomes so thin that the intended effect can not be exhibited. On the other hand, too much of the copolymer results in a high viscosity product which is hard to apply and may give a stiff feeling. The characteristics of films produced by conventional cosmetics are controlled by the addition of camphor, phthalic acid derivative, or alkyd resin. In the cosmetic and personal care composition of the present invention, however, such characteristics can be controlled by adjusting the acrylic chain composition and/or equivalent weight/molecular weight of silicone chain in the copolymer. For example, a hard film can be produced by introducing a large amount of monomers such as methylmethacrylate, t-butyl(meth)acrylate, isobutyl-methacrylate and the like into acrylic chains, while a soft film that is more soluble in a solvent can be produced by using a greater amount of butylacrylate, 2-ethyl hexylacrylate, or mercapto functional silicone; or combination thereof.

A non-aqueous type protective or makeup cosmetic such as insect repellent cream, sunscreen cream, eyeliner, mascara, or the like can be produced by dissolving the vinyl-silicone copolymer into the aforementioned volatile hydrocarbon oil or volatile silicone oil. The volatile component evaporates when this type of makeup cosmetic is applied to the object, thereby producing a continuous film. The amount of copolymer to be incorporated into such a makeup cosmetic composition is usually 0.01–65% by weight, and preferably 0.5–35% by weight. If the amount of copolymer is too small, a continuous film can not be produced, and thus the intended effect can not be adequately exhibited, although this will depend on other components such as waxes or pigments. If the amount of the copolymer is too large, the viscosity becomes so high that the usability of the product is impaired.

Protective and makeup cosmetic compositions can also be prepared by using vinyl-silicone copolymer of the present invention, low- boiling-point oil, a cosmetic material, and a polyacrylic emulsion of the type increasing its viscosity under alkaline conditions. Such a cosmetic composition produces a uniform film which possesses improved water-resistance and produces a thick-film sensation after the application.

Personal hygiene and personal care products such as deodorant, antiperspirants, tooth paste and the like can also be prepared by using vinyl-silicone copolymer of the present invention, low-boiling-point oil, and other necessary ingredients. Such a cosmetic composition provides improved water-resistance and poor adherence of bacteria to such surfaces thereby providing a fresh feeling. Fewer or no stains are observed on teeth in the case of tooth paste.

The aforementioned volatile hydrocarbons or silicone oils having a boiling point below 260° C. at normal pressure can be used as the low-boiling-point oil. They can be used either independently or as a mixture. Their amount in the makeup cosmetic composition is 2–70% by weight, and preferably 5–40% by weight. The low boiling-point oil functions as a solvent of the copolymer. It also plays an important role in spreading and promoting the life of the cosmetic film.

Cosmetic compositions may optionally use other solvents conventionally used in cosmetic formulations, including higher boiling oils and the like. For example, Finsolve TN brand solvent, comercially available from Finetex, Elmwood Park, N.J. provide good delivery and feel properties in cosmetic applications.

There are no specific limitations as to the cosmetic powder material used in the makeup cosmetic composition. It may be a body pigment, inorganic white pigment, inorganic colored pigment, organic pigment, organic powder, pearling agent, or the like. Specific examples are talc, mica, magnesium carbonate, calcium carbonate, magnesium silicate, aluminum magnesium silicate, silica, titanium dioxide, zinc oxide, red iron oxide, yellow iron oxide, black iron oxide, ultramarine blue, tar pigment, nylon powder, polyethylene powder, methacrylate powder, polystyrene powder, polytetrafluoroethylene powder, silk powder, crystalline cellulose, starch, titanated mica, iron oxide titanated mica, bismuth oxychloride, and the like. These cosmetic powder may be used after a surface-treatment with an oily agent such as silicone or the like. They can be used independently, or two or more of them can be used in combination.

The amount of the cosmetic powder material used for the makeup cosmetic composition can be determined depending on the intended use or purpose without limitation. Usually, an amount of 5–40% by weight is preferable.

Polyacrylic emulsions of the type increasing viscosity of the cosmetic composition under alkaline conditions are homopolymers of acrylic acid, or methacrylic acid, their copolymers, and partially cross-linked acrylic acid polymers. They increase the viscosity of cosmetic compositions when neutralized with an alkali. These cosmetic component emulsions may be used independently, or two or more of them can be used in combination. The amount of the composition to be incorporated in the cosmetic composition of the present invention is 1–10% by weight. Within this range, the emulsion component can homogeneously disperse the solution of the vinyl-silicone graft copolymer in the low boiling-point oil in an aqueous phase. If the amount is less than 1% by weight, the dispersion can be achieved only insufficiently, resulting a product having an inadequate viscosity. On the other hand, if the amount is greater than 10% by weight, the product becomes too viscous to be conveniently applied. Any alkaline substance commonly used for cosmetics can be used to neutralize the polyacrylic emulsion and to raise its viscosity. Suitable examples are inorganic alkalies such as sodium hydroxide and potassium hydroxide, basic amino acids such as L-arginine, amines such as triethanolamine, and ammonia, and the like. The amount of alkali used in the cosmetic composition is determined taking into account the type of the alkali and the type of polyacrylic emulsion which are used for preparing the cosmetic composition. Usually, a preferable amount is 0.03–2.5% by weight. The alkali is added, for example, by dissolving it in water, or by directly mixing it with the polyacrylic emulsions. The method of the addition of an alkali, however, is not limited by these.

The cosmetic composition may be in oil-in-water (o/w) type emulsion or water-in-oil (w/o) type emulsion. An o/w and w/o type emulsion cosmetic composition can be prepared by using the copolymer and the low boiling-point oils at specific proportions. These emulsion cosmetic compositions exhibit a smooth spreadability on the skin without imparting an oily sensation, and yet, upon application produce a film having excellent water-repellency. They also possess good stability over time. One or more type of copolymers can be used and incorporated into these emulsions.

The non-aqueous type makeup cosmetic composition of the present invention can be prepared by blending the above components according to a conventional method and can be prepared into various forms, including a cream, and a liquid in which the cosmetic powder materials are homogeneously dispersed or precipitated. The cosmetic composition is applied to foundation, eyeshadows, rouges, face powders, and the like.

The oil-in-water type emulsion cosmetic composition comprises 1–50% by weight of an oily component mixture which comprises 1–40% by weight of the copolymer and 2–60% by weight of the low boiling-point oil, wherein the amount of vinyl-silicone copolymer plus low boiling-point oil in the total oily component mixture is 5–100% by weight. The vinyl-silicone copolymer plays an important role in the high water-repellency possessed by the o/w type emulsion cosmetic composition. The amount of this copolymer in the oily component mixture is in the range of 1–40% by weight. An amount of less than 1% by weight does not produce a sufficient water-repelling characteristics in the emulsion cosmetic composition. An amount exceeding 40% by weight of the copolymer in the mixture raises the viscosity of the resulting emulsion cosmetic composition. This affects the readiness in the application of the emulsion cosmetic composition to the skin and imparts an oily feeling to the skin. The aforementioned low boiling-point oils can be used for the oily component mixture for producing an o/w type emulsion cosmetic composition. They may be used independently or two or more of them can be used in combination. The low boiling-point oil dissolves the copolymer, thereby producing a homogeneous oil phase. After application of the emulsion cosmetic composition, it evaporates leaving a good cosmetic film on the skin. The amount of the low boiling-point oil in the oil component mixture is suitably determined taking into account the amount of copolymer and other factors. Usually, the preferable amount is 2–60% by weight. If the amount is smaller than 2% by weight, the resulting cosmetic composition in which a comparatively large amount of the copolymer is incorporated exhibits only poor spreadability and imparts an oily feeling upon use. If greater than 60% by weight, a longer time is required for the emulsion cosmetic composition to be fixed and the cosmetic composition tends to leave a thin film after makeup. The total amount of the vinyl-silicone copolymer and the low-boiling-point oil in the oil component mixture is 5–100% by weight and preferably 10–60% by weight. If the amount is smaller than 10% by weight, the water repellency and the excellent feeling upon use of the resulting emulsion cosmetic composition are lost.

Oil components other than the vinyl-silicone copolymer, and the low boiling-point oil which can be used for the oil component mixture for producing the emulsion cosmetic composition of the present invention may be liquid, semisolid, or solid oils. Specific examples include liquid, paste, or solid hydrocarbons such as liquid paraffin, squalane, and the like; waxes, higher fatty acids, higher alcohols, esters, glycerides, low and high molecular weight silicone oils, and the like. These oil components may be used independently or two or more of them can be used in combination. They form a homogeneous oil phase together with the copolymer and low boiling-point oil. They also function as a plasticizer in the formation of a resin by the copolymer when the low boiling-point oil evaporates. The oil component mixture containing a low-viscosity silicone oil is particularly preferable. The stability of the cosmetic composition and the feeling upon use can be remarkably promoted by the use of such a component mixture.

The oil component mixture comprising the above components is used in the o/w type emulsion cosmetic composition of the present invention in an amount of 5–40% by weight. If the amount is smaller than 5% by weight, a sufficient water repelling effect can not be obtained. On the other hand, if the amount is greater than 40% by weight, the stability of the emulsion cosmetic composition tends to be impaired.

The oil-in-water type emulsion cosmetic composition can be prepared by emulsifying the oil phase and the water phase according to a conventional method. It can be made into a cream, lotion or the like.

A makeup cosmetic composition comprising the vinyl-silicone graft copolymer, a low-viscosity silicone oil and/or a low boiling-point oil, and a cosmetic powder material is an another embodiment of the present invention. This makeup cosmetic composition has excellent water-repellency, oil-resistance, and water-resistance. It gives a good feeling upon use, and its makeup effect lasts for a long period.

Makeup cosmetic compositions can easily be prepared by utilizing the components already described above. Among this type of makeup cosmetic composition, a non-aqueous type makeup cosmetic composition comprising 0.03–40% by weight of the vinyl-silicone graft copolymer, 1–60% by weight of the low-viscosity silicone oil, 5–80% by weight of a volatile hydrocarbon, and 5–50% by weight of a cosmetic powder material is preferable composition. It has an excellent stability, water or sweat resistance, gives a good feeling upon use, and yet possesses improved oil or sebum resistance and friction resistance.

The vinyl-silicone graft copolymer is incorporated into the cosmetic composition in an amount of 0.03–40% by weight. If less than 0.03% by weight, the intended effect can not be obtained. If greater than 40% by weight, the cosmetic film produced gives a thick feeling.

The aforementioned low-viscosity silicone oil can be used in an amount of 1–60% by weight. If the amount of low boiling point silicone oil is less than 1% by weight, the result is a film with insufficient softness. On the other hand, with the amount exceeding 60% by weight, a long period of time is required for the makeup to "fix" after application. The resulting cosmetic film from a composition containing too much silicone oil is so thin that it gives an unsatisfactory feeling to the user.

The volatile hydrocarbons of the type previously mentioned when used in the cosmetic composition maintain the vinyl-silicone copolymer in a well-dissolved condition. After the cosmetic composition is applied to the skin, the solvent evaporates and a good cosmetic film is formed which lasts over a long period of time. It is desirable that the volatile hydrocarbon be incorporated in an amount of 5–80% by weight. If the amount is smaller than 5% by weight, the cosmetic composition produced has a higher viscosity and does not spread well over the skin when applied. This leads to difficulty in forming a homogeneous film.

It is desirable that the cosmetic powder material be added in an amount of 5–50% by weight of the total amount of the cosmetic composition. The specific amount depends on the intended use and intended application of the cosmetic composition.

As still another embodiment, the present invention provides a water-in-oil type emulsion cosmetic composition comprising 0.3–30% by weight of a vinyl-silicone graft copolymer, 15–75% by weight of a low-viscosity silicone oil and/or a low-boiling-point oil, 0.1–10% by weight of a surface active agent, and 5–70% by weight of water. In this composition the preferred total amount of vinyl-silicone copolymer plus low-viscosity silicone oil and/or low-boiling-point oil is 15–60% by weight. This w/o type emulsion cosmetic composition has good stability over time, produces a film exhibiting a superior water-repellency, and gives an excellent feeling upon use. One or more types of the vinyl-silicone copolymers can be used and incorporated into the w/o type emulsion cosmetic composition in an amount of 0.3–30% by weight. An amount smaller than 0.3% by weight does not give the sufficient intended effect. If the amount of the copolymer exceeds 30% by weight, the resulting cosmetic composition gives a heavy feeling to the skin when applied. In addition, an oily feeling impairs the use value of the product.

The above mentioned low-viscosity silicone oil and low-boiling-point oil can be used in this w/o type emulsion cosmetic composition. The total amount of the low-viscosity silicone oil and low-boiling-point oil is 15–60% by weight of the cosmetic composition. If the amount is less than 15% by weight, and especially the amount of the low-viscosity silicone oil is too small, a smooth, water-repellent characteristic can not be exhibited effectively.

Besides the above defined components, synthetic or natural cosmetic oils conventionally used for cosmetics can be incorporated to the extent that the homogeneity of the oil phase is not adversely effected.

The vinyl-silicone copolymer and the low-viscosity silicone oil and/or the low-boiling-point oil are incorporated into the w/o type emulsion cosmetic composition in an amount of 5–60% by weight in total.

Oxyalkylene-modified organosiloxane type surface active agents which can emulsify water into the oily components of the cosmetic composition can be used as additional components without any special restriction. Oxyalkylene-modified organosiloxanes include polyether-modified silicones, and alkyl-polyether-modified silicones. Organosiloxanes shown below are presented as examples and are not limited by any means.

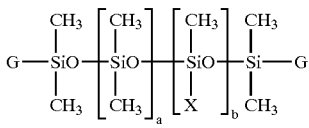

wherein G represents $CH_3$, or $(CH_2)_p O(C_2H_4O)_m(C_3H_6O)_n R_a$, or $(OC_2H_4)_m(OC_3H_6)_n OR_b$, wherein p is 1–5, m is 1–50 and n is 0–30; $R_a$ and $R_b$ represents a hydrogen atom or an alkyl group having 1–5 carbon atoms; X represents $(CH_2)_p O(C_2H_4O)_m(C_3H_6O)_n R_a$, or $(OC_2H_4)_m(OC_3H_6)_n OR_b$ wherein p, m, and n have the same meaning as defined above; a is 1–300, and preferably 1–30; and b is 1–350, and preferably 1–50. Each G and X can be same or different in a molecule. Moieties represented by repeating units a and b may also be present in a random fashion.

Organosiloxane surfactants that are liquid or paste at normal temperature and are water-insoluble are preferable. Specific examples are Silwet® L-722, and L-7500 surfactants (trade-mark, Union Carbide Corporation), Silicone KF-945 surfactant (trade mark, Shin-Etsu Chemical Co., Ltd.), Silicone SH-3772C surfactant (trade mark, Toray Silicone Co., Ltd.), and the like. Since such an oxyalkelene-modified organopolysiloxane has a polysiloxane as the main chain, its mutual solubility with the vinyl-silicone graft copolymer, low-viscosity silicone oil, and low-boiling-point oil is excellent. This contributes to the formation of a stable emulsion.

An amount of 0.1–10% by weight, preferably of 0.5–5% by weight, of the surface active agent is incorporated into the w/o type emulsion cosmetic composition. If the amount is less than 0.1% by weight, a sufficient emulsification effect can not be exhibited. An amount exceeding 10% by weight tends to make the resulting product feel heavy and sticky.

Water is incorporated in an amount of 5–70% by weight as one of the components.

In the preparation of the w/o type emulsion cosmetic composition, the vinyl-silicone graft copolymer, low-viscosity silicone oil, and/or low-boiling-point oil are dissolved in advance. Otherwise, a process conventionally used for the production of a w/o type emulsion cosmetic can be used for the preparation of the composition.

Hair Care Compositions

The vinyl-silicone copolymers as described herein are used in hair care products in an amount of 0.01 to 30% by weight, and preferably 0.1 to 10% by weight in well-known compositions such as shampoos, rinses, hair treatment products, hair setting products, cold permanent wave lotions or the like. The hair care products into which the copolymer is incorporated may be of any form, such as liquid, cream, emulsion, gel or the like. It may also be used in combination with well-known conventional naturally occurring polymers, modified products of naturally occurring polymers, or synthetic polymers.

Hair care products in which the copolymer in accordance with the present invention is used include hair conditioning compositions such as shampoos, rinses, hair grooming products such as hair treatment lotions, cold permanent wave lotions and the like for providing hair with softness, gloss, smooth combing, recovery from damage, manageability, and the like and those for providing hair setting compositions for setting hair in desired hair style such as aerosol hair sprays, pump hair sprays, foaming type hair sprays, hair mists, hair setting lotions, hair styling gels, hair liquids, hair creams, hair oils and the like.

The compositions of the invention also comprise a carrier, or a mixture of such carriers, which are suitable for application to hair. The carriers are present at from about 0.5% to about 99.5%, preferably from about 5.0% to about 99.5%, and most preferably from about 10% to 90.0%, of the composition. As used herein, the phrase "suitable for application to hair" means that the carrier does not damage or negatively affect the aesthetics of hair or cause irritation to skin. Choice of appropriate solvent will also depend on the particular copolymer to be used, and whether the product formulated is meant to be left on hair (e.g., hair sprays, mousse, tonic) or rinsed off (e.g., shampoo, conditioner) after use.

The carrier used herein include solvents, as well as other carrier or vehicle components conventionally used in hair care compositions. The solvent selected must be able to dissolve or disperse the particular silicone copolymer being used. The nature and proportion of monomer in the copolymer largely determines the copolymer's polarity and solubility characteristics. The silicone copolymers can be designed, by appropriate selection of monomers, for formulation with a wide range of solvents. Suitable solvents for use in the present invention include, but are not limited to, water; lower alcohols such as ethanol or isopropanol; hydroalcoholic mixtures; hydrocarbons such as isobutane, hexane, decane or acetone; halogenated hydrocarbons such as Freon™ fluorocarbons; hydrocarbon esters such as ethyl acetate and dibutyl phthalate; volatile silicone derivatives, especially siloxanes, such as phenyl pentamethyl disiloxane, methoxypropyl heptamethyl cyclotetrasiloxane, chloropropyl pentamethyl disiloxane, hydroxypropyl pentamethyl disiloxane, octamethyl-cyclotetrasiloxane, and decamethyl cyclopentasiloxane; and mixtures thereof. The solvents used in such mixtures may be miscible or immiscible with each other.

The copolymers in accordance with the present invention are used in these hair care products as a partial or total substitute for or in combination with anionic, nonionic, cationic, and amphoterid polymers, and polysiloxane polymers conventionally used in these hair care products.

The hair care compositions in accordance with the present invention may be formulated in a wide variety of product types, including mousses, gels, lotions, tonics, sprays, shampoos, and conditioners. The additional components required to formulate such products vary with product type and can be routinely chosen by one skilled in the hair care product art.

The hair care compositions of the present invention are used in conventional ways to provide the hair conditioning/styling/hold benefits of the present invention. The method of use depends upon the type of composition employed but generally involves application of an effective amount of the product to the hair, which may then be rinsed from the hair (as in the case of shampoos and some conditioning products), or allowed to remain on the hair (as in the case of spray, mousse, gel, and tonic products). By effective amounts is meant an amount sufficient to provide the hair conditioning/styling/hold benefits desired considering the length and texture of the hair, and the type of the product used.

The cosmetic composition provided by the present invention can be applied to a wide variety of uses such as for basic cosmetics, makeup cosmetics, hair cosmetics, and the like. Besides the above components, various components conventionally used for cosmetics can be optionally incorporated into the cosmetic composition of the present invention to the extent that such incorporation does not impair the intended effects of the cosmetic composition. Such optional components include alkali metal soaps, polyhydric alcohols, high molecular weight compounds, preservatives, alkaline agents, UV absorbers, anti-oxidants, tar-derived coloring agents, skin-improvers, humectants, perfumes, and the like.

The present invention is explained more specifically with reference to the following preparation examples and formulation examples without limit thereto. The parts and percentages in the preparation examples are represented by weight. The parts and percentages in the formulation examples are represented by weight on the basis of effective components.

EXAMPLES

Examples 1–8 were prepared by a general method as described below.

A 250 ml three-necked flask was fitted with a magnetic stirrer, a condenser, a thermometer, a stopper, and a nitrogen inlet. The reaction apparatus was flushed with nitrogen. All the desired monomers, solvent and initiator were charged into the flask, and nitrogen was bubbled through the reaction mixture for ~15 minutes. Polymerization was carried out by heating this reaction mixture at desired temperature for desired hours under positive pressure of nitrogen. Removal of solvent gave a solid polymer.

The mercapto functional silicone compound used in Example 1–8 are pendant functional mercaptopolydimethylsiloxanes of 100–200 centistokes viscosity with 5–10 mole % of 3-mercaptopropylmethylsiloxane unit and were obtained from Huls America, Inc (catalog # PS850).

Example 1

Preparation of copolymer using Mercapto Functional Silicone (PS850), Acrylic Acid(AA), and n-Butyl Methacrylate (NBM)

To a mixture of 30 parts of PS850, 10 parts of AA, and 60 parts of NBM in 150 parts of methyl ethyl ketone (MEK) was added 0.25 parts (of monomers) of 2,2'-azobisisobutyronitrile (AIBN). This solution was purged with nitrogen and reaction was carried out at 60° C. for 18 hours. Polymer was recovered by evaporation of solvent.

Example 2

Preparation of Copolymer using Mercapto Functional Silicone (PS850), Acrylic Acid(AA), and t-Butyl Acrylate (TBA)

To a mixture of 20 parts of PS850, 20 parts of AA, and 60 parts of TBA in 150 parts of methyl ethyl ketone (MEK) was added 0.25 parts (of monomers) of 2,2'-azobisisobutyronitrile (AIBN). This solution was purged with nitrogen and reaction was carried out at 60° C. for 18 hours. Polymer was recovered by evaporation of solvent.

Example 3

Preparation of Copolymer using Mercapto Functional Silicone (PS850), Ethylhexyl methacrylate (EHM), and i-Butyl Methacrylate (IBM).

To a mixture of 30 parts of PS850, 30 parts of EHM, and 40 parts of IBM in 150 parts of methyl ethyl ketone (MEK) was added 0.25 parts (of monomers) of 2,2'-azobisisobutyronitrile (AIBN). This solution was purged with nitrogen and reaction was carried out at 60° C. for 18 hours. Polymer was recovered by evaporation of solvent.

Example 4

Preparation of Copolymer using Mercapto Functional Silicone (PS850), N-vinyl pyrrolidone (NVP), and i-Butyl Methacrylate (IBM).

To a mixture of 30 parts of PS850, 20 parts of NVP, and 50 parts of IBM in 150 parts of methyl ethyl ketone (MEK) was added 0.25 parts (of monomers) of 2,2'-azobisisobutyronitrile (AIBN). This solution was purged with nitrogen and reaction was carried out at 60° C. for 18 hours. Polymer was recovered by evaporation of solvent.

Example 5

Preparation of Copolymer using Mercapto Functional Silicone (P8850), N,N-Dimethylacrylamide (DMA), and i-Butyl Methacrylate (IBM).

To a mixture of 25 parts of PS850, 10 parts of DMA, and 65 parts of IBM in 150 parts of methyl ethyl ketone (MEK) was added 0.25 parts (of monomers) of 2,2'-azobisisobutyronitrile (AIBN). This solution was purged with nitrogen and reaction was carried out at 60° C. for 18 hours. Polymer was recovered by evaporation of solvent.

Example 6

Preparation of Copolymer using Mercapto Functional Silicone (PS850), N,N-(Dimethylamino)ethyl Methacrylate (DMAEMA), and i-Butyl Methacrylate (IBM).

To a mixture of 20 parts of PS850, 10 parts of DMAEMA, and 70 parts of IBM in 150 parts of methyl ethyl ketone (MEK) was added 0.25 parts (of monomers) of 2,2'-azobisisobutyronitrile (AIBN). This solution was purged with nitrogen and reaction was carried out at 60° C. for 18 hours. Polymer was recovered by evaporation of solvent.

Example 7

Preparation of Copolymer using Mercapto Functional Silicone (PS850), and i-Butyl Methacrylate (IBM).

To a mixture of 30 parts of PS850, and 70 parts of IBM in 150 parts of methyl ethyl ketone (MEK) was added 0.25 parts (of monomers) of 2,2'-azobisisobutyronitrile (AIBN). This solution was purged with nitrogen and reaction was carried out at 60° C. for 18 hours. Polymer was recovered by evaporation of solvent.

Example 8

Preparation of Copolymer using Mercapto Functional Silicone (PS850), and t-Butyl Acrylate (TBA).

To a mixture of 20 parts of PS850, and 80 parts of TBA in 150 parts of methyl ethyl ketone (MEK) was added 0.25 parts (of monomers) of 2,2'-azobisisobutyronitrile (AIBN). This solution was purged with nitrogen and reaction was carried out at 60° C. for 18 hours. Polymer was recovered by evaporation of solvent.

Examples 9–15 were prepared by the same general procedure as described below.

A 16 oz narrow-mouth glass bottle was charged with the monomers, solvent, and initiator. The reaction solution was deoxygenated by bubbling the nitrogen gas for 5–10 minutes. The bottle was then sealed with a foiled lined cap. The polymerizations were carried out in an Atlas Launder-O-Meter™ for 24 hrs.

The mercapto functional silicone compound used in Example 9–15 are pendant functional, mercaptopolydiorganosiloxane of 100–200 centistokes viscosity with 5–10 mole% of 3-mercaptopropylmethylsiloxane unit and were obtained from Shin-Etsu, Inc (catalog # KF2001).

Example 9

Preparation of Copolymer using Mercapto Functional Silicone (KF2001), and Methyl Methacrylate (MMA).

To a mixture of 10 parts of KF2001, and 90 parts of MMA in 100 parts of ethyl acetate (EtOAc) was added 0.1 parts (of monomers) of 2,2'-azobisiso-butyronitrile (AIBN). This solution was purged with nitrogen and reaction was carried out at 60° C. for 24 hours. Polymer was recovered by evaporation of solvent.

Example 10

Preparation of Copolymer using Mercapto Functional Silicone (KF2001), and Ethyl Methacrylate (EMA).

To a mixture of 10 parts of KF2001, and 90 parts of EMA in 100 parts of ethyl acetate (EtOAc) was added 0.1 parts (of monomers) of 2,2'-azobisiso-butyronitrile (AIBN). This solution was purged with nitrogen and reaction was carried out at 60° C. for 24 hours. Polymer was recovered by evaporation of solvent.

Example 11

Preparation of Copolymer using Mercapto Functional Silicone (KF2001), and t-Butyl Acrylate (TBA).

To a mixture of 10 parts of KF2001, and 90 parts of TBA in 100 parts of ethyl acetate (EtOAc) was added 0.1 parts (of monomers) of 2,2'-azobisiso-butyronitrile (AIBN). This solution was purged with nitrogen and reaction was carried-.out at 60° C. for 24 hours. Polymer was recovered by evaporation of solvent.

Example 12

Preparation of Copolymer using Mercapto Functional Silicone (KF2001), and i-Butyl Methacrylate (IBM).

To a mixture of 10 parts of KF2001, and 90 parts of IBM in 100 parts of ethyl acetate (EtOAc), was added 0.1 parts (of monomers) of 2,2'-azobisiso-butyronitrile (AIBN). This solution was purged with nitrogen and reaction was carried out at 60° C. for 24 hours. Polymer was recovered by evaporation of solvent.

Example 13

Preparation of Copolymer using Mercapto Functional Silicone (KF2001), and n-Butyl Methacrylate (NBM).

To a mixture of 10 parts of KF2001, and 90 parts of NBM in 100 parts of ethyl acetate (EtOAc) was added 0.1 parts (of monomers) of 2,2'-azobisiso-butyronitrile (AIBN). This solution was purged with nitrogen and reaction was carried out at 60° C. for 24 hours. Polymer was recovered by evaporation of solvent.

Example 14

Preparation of Copolymer using Mercapto Functional Silicone (KF2001), i-Butyl Methacrylate (IBM), and Acrylic Acid(AA).

To a mixture of 10 parts of KF2001, 10 parts of AA, and 80 parts of IBM in 100 parts of ethyl acetate (EtOAc) was added 0.1 parts (of monomers) of 2,2'-azobisisobutyronitrile (AIBN). This solution was purged with nitrogen and reaction was carried out at 60° C. for 24 hours. Polymer was recovered by evaporation of solvent.

Example 15

Preparation of Copolymer using Mercapto Functional Silicone (KF2001), i-Butyl Methacrylate (IBM), and N,N-Dimethyl Acrylamide (DMA).

To a mixture of 10 parts of KF2001, 10 parts of DMA, and 80 parts of IBM in 100 parts of ethyl acetate (EtOAc) was added 0.1 parts (of monomers) of 2,2'-azobisisobutyronitrile (AIBN). This solution was purged with nitrogen and reaction was carried out at 60° C. for 24 hours. Polymer was recovered by evaporation of solvent.

Example 16

Preparation of copolymer using mercapto functional silicone (KF2001), acrylic acid (AA), and i-butyl methacrylate (IBM).

To a mixture of 30 parts of KF2001, 10 parts of acrylic acid, and 60 parts of IBM in 100 parts of ethyl acetate (EtOAc) was added 0.1 parts (of monomers) of 2,2'-azobisisobutyronitrile (AIBN). This solution was purged with nitrogen and reaction was carried out at 60° C. for 24 hours.

Example 17

Preparation of copolymer using mercapto functional silicone (KF2001), methacrylic acid (MAA), and i-butyl methacrylate (IBM).

To a mixture of 30 parts of KF2001, 10 parts of MA, and 60 parts of IBM in 100 parts of ethyl acetate (EtOAc) was added 0.1 parts (of monomers) of 2,2'-azobisisobutyronitrile (AIBN). This solution was purged with nitrogen and reaction was carried out at 60° C. for 24 hours.

Example 18

Preparation of copolymer using mercapto functional silicone (KF2001), acrylic acid (AA), ethylhexyl methacrylate (EHM), and i-butyl methacrylate (IBM).

To a mixture of 30 parts of KF2001, 10 parts of AA, 20 parts of EHM, and 40 parts of IBM in 100 parts of ethyl acetate (EtoAc) was added 0.2 parts (of monomers) of 2,2'-azobisisobutyronitrile (AIBN). This solution was purged with nitrogen and reaction was carried out at 60° C. for 24 hours.

Example 19

Preparation of copolymer using mercapto functional silicone (KF2001), methacrylic acid (MAA), ethylhexyl methacrylate (EHM), and i-butyl methacrylate (IBM).

To a mixture of 30 parts of KF2001, 10 parts of MAA, 20 parts of EHM, and 40 parts of IBM in 100 parts of ethyl acetate (EtOAc) was added 0.1 parts (of monomers) of 2,2'-azobisisobutyronitrile (AIBN). This solution was purged with nitrogen and reactions was carried out at 60° C. for 24 hours.

Example 20

To 61.1 g of water, 0.95 g ammonium hydroxide solution of 29.9% concentration was charged. This solution was added to 13.1 g reaction mixture of Example 16 in a round bottomed flask. Ethyl acetate was removed on rotary evaporator to give a hazy solution of 10% concentration.

Example 21

To 61.1 g of water, 0.95 g ammonium hydroxide solution of 29.9% concentration was charged. This solution was added to 13.1 g reaction mixture of Example 17 in a round bottomed flask. Ethyl acetate was removed on rotary evaporator to give a slightly hazy solution of 10% concentration.

Example 22

To 21.03 g of the polymer of Example 19 was added 58.07 g water and 1.43 g ammonium hydroxide solution (29.9%). Ethyl acetate was removed on rotary evaporator to give a hazy solution of 15% concentration.

Example 23

To 113 g of reaction mixture of the polymer of Example 17 was added 6.16 g of 2-amino-2-methyl-1-propanol (AMP) followed by addition of 219.8 g water. Ethyl acetate was removed on rotary evaporator to give a hazy solution of 20 wt % concentration.

Example 24

To 77.5 g of water, 2.51 g ammonium hydroxide solution of 29.9% concentration was charged. This solution was added to 28.24 g reaction mixture of Example 17 in a round bottomed flask. Ethyl acetate was removed on rotary evaporator to give a slightly hazy solution of 15% concentration.

Example 25

To 30.12 g of water, 1.40 g ammonium hydroxide solution of 29.9% concentration was charged. This solution was added to 15.54 g reaction mixture of Example 17 in a round bottomed flask. Ethyl acetate was removed on rotary evaporator to give a slightly hazy solution of 20% concentration.

Example 26

To 10 g solution of Example 25 was added 30 g of ethanol to give a hair spray formulation with 5% polymer with ethanol/water ratio of 80/20. When sprayed on hair, it gave softness to hair without limpness.

Example 27

A face cream composition representative of the present invention is prepared using the following formulation.

| | |
|---|---|
| Mineral Oil | 15.00 |
| Cetyl Alcohol | 2.00 |
| Lanolin | 2.00 |
| Arlacell 165 Emulsifier[1] | 10.00 |
| Tween 60 Surfactant[1] | 1.00 |
| Glycerine | 6.00 |
| Octamethylcyclotetrasiloxane | 10.00 |
| Polymer of Example 3 | 2.00 |
| Water | 52.00 |
| | 100.00 |

[1]Available from ICI Americas

Example 28

A nail polish composition representative of the present invention is prepared using the following formulation.

| | |
|---|---|
| D4 | 21.50 |
| Propylene Glycol | 2.00 |
| Ethoxylan 50[1] | 1.00 |
| SD-Alcohol 40[2] | 55.00 |
| Polymer of Example 4 | 20.00 |
| D&C Red #22 | 0.50 |
| | 100.00 |

[1]Available from Emery PCPG
[2]SD Alcohol 40 is ethyl alcohol denatured with brucine, brucine sulfate, or quassin, and t-butyl alcohol.

The following polymer of formulations are prepared for their use in subsequent compositions.

Formulation #1

5 Gram of copolymer prepared in Example 14 was dissolved in 50 ml of 200 proof ethyl alcohol. After the polymer is dissolved, 1.25 g (equimolar amount to acid) of 2-amino 2-methyl-1-propanol (AMP) was added to it. The formulation thus obtained is referred to as F-1.

Formulation #2

6.4 Gram of copolymer prepared in Example 2 was dissolved in 50 ml of 200 proof ethyl alcohol. After the polymer is dissolved, 1.61 g (equimolar amount to acid) of AMP was added to it. The formulation thus obtained is referred to as F-2.

Formulation #3

20 Gram of the copolymer prepared in Example 8 was taken in 100 ml of isopropanol and 80 g of octamethylcyclotetrasiloxane($D_4$). Isopropanol is removed from the mixture on rotary evaporator providing a gel composition which is a uniform jelly. This composition is usable in cosmetic formulations. The formulation thus obtained is referred to as F-3.

Formulation #4

20 Gram of the copolymer prepared in Example 3 was taken in 100 ml of isopropanol and 80 g of octamethylcyclotetrasiloxane($D_4$). Isopropanol is removed from the mixture on rotary evaporator providing a gel composition which is a uniform jelly. This composition is usable in cosmetic formulations. The formulation thus obtained is referred to as F-4.

Formulation #5

20 Gram of the copolymer prepared in Example 7 was taken in 100 ml of isopropanol and 100 g of octamethylcyclotetrasiloxane($D_4$). Isopropanol is removed from the mixture on rotary evaporator providing a gel composition which is a uniform solid. This composition is usable in cosmetic formulations. The formulation thus obtained is referred to as F-5.

Formulation #6

In a 250 ml round-bottomed flask was charged 50 g of copolymer solution of Example 4 and 60 g of Finsolv TN brand solvent (obtained from Finetex Inc.). Methyl ethyl ketone (MEK) was removed from this solution on a rotary evaporator to give a 25% solution of the polymer in Finsolv solvent. The composition is useable in cosmetic formulations. The formulation thus obtained is referred to as F-6.

Formulation #7

The procedure of Formulation #6 was repeated utilizing the polymer solution of Example 5. This composition is useable in cosmetic formulations. The formulation thus obtained is referred to as F-7.

Formulation #8

The procedure of Formulation #6 was repeated utilizing the polymer solution of Example 7. The composition is useable in cosmetic formulations. The formulation thus obtained is referred to as F-8.

Example 29

A lip gloss composition representative of the present invention is prepared using the following formulation.

| | |
|---|---|
| Beeswax | 25.00 |
| Drakeol 7 Mineral Oil[1] | 20.00 |
| Isopropyl Myristate | 10.00 |
| Penreco Snow Petrolatum | 20.00 |
| F-5 | 25.00 |
| | 100.00 |

[1]Available from Penreco

Example 30

A stick eyeshadow composition of the present invention is prepared using the following formulation.

| | |
|---|---|
| F-5 | 85.00 |
| Phenethylpentamethyldisiloxane | 5.00 |
| Colored Pigments | 4.50 |
| Titanated Mica | 3.5 |
| Mica | 2.00 |
| | 100.00 |

Example 31

After-shave conditioning lotion representative of the present invention is prepared by using the following formulation.

| | |
|---|---|
| Ethanol (anhydrous) | 91.00 |
| Water | 5.00 |
| F-2 | 2.00 |
| Fragrance | qs |

Example 32

The shampoo composition, representative of the present invention was prepared using the following formulation.

| | |
|---|---|
| Sodium Laureth-7-sulphate | 16% |
| Lauroyl Diethanolamide | 2.0% |
| F-1 | 0.5% |
| DI Water | balance |
| | 100% |

When the composition was used for shampooing, hair after washing combed smoothly, and the hair after drying had an excellent gloss and brilliance and a smooth feeling.

Example 33

The shampoo composition, representative of the present invention was prepared using the following formulation.

| | |
|---|---|
| Sodium Laureth-7-sulphate | 16% |
| Lauroyl Diethanolamide | 2.0% |
| F-2 | 0.5% |
| DI Water | balance |
| | 100% |

When the composition was used for shampoos, excellent effects as in Example 16 were obtained.

Example 34

The rinse composition, representative of the present invention was prepared using the following formulation.

| | |
|---|---|
| Variquat 638 | 2.0% |
| Lauroyl Diethanolamide | 2.0% |
| F-2 | 0.5% |
| DI Water | balance |
| | 100% |

Variquat 638 is a quaternary ammonium compound and is commercially available from Sherex Chemical Company, Inc.

When the composition was used for a rinse, hair After rinsing was combed smoothly, and the hair after drying had an excellent gloss and brilliance, and a smooth feeling so that the hair was combed smoothly.

Example 35

The rinse composition representative of the present invention was prepared by using the following formulation.

| | |
|---|---|
| Variquat 638 | 2.0% |
| Lauroyl Diethanolamide | 2.0% |
| Silicone Oil (10,000 mol. wt.) | 0.5% |
| F-2 | 0.5% |
| DI Water | balance |
| | 100% |

Variquat 638 is a quaternary ammonium compound and is commercially available from Sherex Chemical Company, Inc.

When the composition was used for hair rinse, excellent effects as in Example 18 were obtained.

Example 36

The rinse composition representative of the present invention was prepared by using the following formulation.

| | | |
|---|---|---|
| Variquat 638 | 2.0% | |
| Lauroyl Diethanolamide | 2.0% | |
| F-1 | 0.5% | |
| DI Water | balance | |
| | 100% | |

Variquat 638 is a quaternary ammonium compound and is commercially available from Sherex Chemical Company, Inc.

When the composition was used for hair rinse, excellent effects as in Example 18 were obtained.

Examples 37–41

The hair spray compositions representative of the present invention were prepared as follows.

Copolymers of Example 2, Example 4, Example 13, Example 14, and Example 15 were dissolved in ethyl alcohol to give 5% solution. Formulations were tested by spraying the polymer solution on to hair swatches with a pump. When these formulations were used by spraying them onto hair, they gave very good set maintaining the hold capability as well as a smooth feeling.

Example 42

A hair oil composition representative of the present invention was prepared using the following formulation.

| | |
|---|---|
| D4 | 40.00 |
| F-2 | 5.00 |
| Anhydrous Ethanol | balance |
| | 100.00 |

Example 43

An anti-perspirant composition representative of the present invention is prepared using the following formulation.

| | |
|---|---|
| [1]Bentonite Gel Rheological additive | 8.0 |
| [2]Arlamol E Emollient | 3.0 |
| F-4 | 3.0 |
| [2]Arlacel 80 Emulsifier | 0.50 |
| [3]Macrospherical 95 Antiperspirant | 6.00 |
| [4]Propellant A-46 | balance |
| | 100.00 |

[1]commercially available from NL Industries, Inc.
[2]commercially available from ICI Americas, Inc.
[3]commercially available from Reheis Chemical Co.,
[4]hydrocarbon propellant available from Phillips Chemical Co.

[1]commercially available from NL Industries, Inc.
[2]commercially available from ICI Americas, Inc.
[3]commercially available from Reheis Chemical Co.,
[4]hydrocarbon propellant available from Phillips Chemical Co.

Example 44

A toothpaste composition representative of the present invention is prepared using the following formulation.

| | |
|---|---|
| Tricalcium phosphate | 51.8 |
| Propylene Glycol | 40.0 |
| F-1 | 5.5 |
| Sodium Lauryl Sulphate | 1.8 |
| Flavoring | 0.9 |
| | 100.00 |

Example 45

A hand cream composition representative of the present invention is prepared using the following formulation:

| | | |
|---|---|---|
| A | Polyglyceryl-3-distearate (Cremophor GS 32)[1] | 3.00 |
| | Finsolv TN brand solvent | 8.00 |
| | F-6 or F-7 or F-8 | 2.00 |
| | (Cetearyl alcohol (Lanette O)[2] | 3.00 |
| B | Propylene glycol | 5.00 |
| | water | 79.00 |
| C | Germaben II | q.s |
| | Fragrance | q.s |

[1]BASF Corp.
[2]Henkel Inc.

Heat A and B, separately to 75–80° C. Add B to A with stirring and homogenize. Cool with stirring and add C at 35° C.

Preferred polymers and hair care compositions containing them were prepared as follows:

Example 46

Into a 16 ounce reaction vessel was charged 20 grams of methylacrylate (MA), 50 g of methyl methacrylate (MMA), 10 grams of methacrylic acid (MAA), 30 g of mercapto-functional silicone, KF2001, available from Shin-Etsu, 165 g of methyl ethyl ketone and 0.55 grams of 2',2'-azobisisobutyronitrile (AIBN). The mixture was purged with nitrogen for 2 minutes at 1 L/min, after which the bottle was sealed. The sealed vessel containing the clear solution was tumbled in a constant temperature bath at 55° C. for about 48 hrs, resulting in a viscous clear solution.

Example 47

The procedure of Example 46 was repeated. The charges of components were as follows: MA(50 g), MMA(20 g), MAA(5 g), KF2001 (25 g), methyl ethyl ketone (150 g), AIBN (0.5 g).

The solution was tumbled in a constant temperature bath for 24 hours at 55° C.

Example 48

The procedure of Example 46 was repeated. The charges of components were as follows: MA(30 g), MMA(40 g), MAA(10 g), KF2001 (30 g), methyl ethyl ketone (165 g), AIBN (0.55 g).

The solution was tumbled in a constant temperature bath for 44 hours at 55° C.

WATERBORNE ANALOGUES OF EXAMPLES 46–48

Example 49

In a 250 ml round bottom flask was charged 90 grams deionized (DI) water and 0.643 grams NH$_4$OH (30% solution). Thereafter, 25.6 grams of solvent borne solution (39.0% solids) prepared in Example 46 added to the solution in the flask. The resulting solution was placed on a shaker and shaken for one-half hour in order to complete the neutralization. The MEK was thereafter stripped from the resulting viscous solution on a rotary evaporator at 40° C. using an aspirator vacuum to yield 10.0% solids.aqueous solution.

Example 50

The procedure of Example 49 was repeated. The charges of components are as follows: DI $H_2O$ (90 g), $NH_4OH$ solution (0.354 g), 25 g of solvent borne solution as prepared in Example 49.

Example 51

The procedure of Example 49 was repeated. The charges of components are as follows: DI $H_2O$ (90 g), $NH_4OH$ solution (0.707 g), 25 g of solvent borne solution as prepared in Example 48.

Comparative Example

To illustrate the beneficial properties of polymers of the present invention, various compositions were tested for dry film characteristics, hair tress combability after spraying and drying, and curl retention under 93% relative humidity conditions. The materials tested were the compositions of Example 49 and a National Starch "Non-Aerosol Styling Mist" base prepared with AMP neutralized Amphomer LV-71. LV-71 is an amphoteric acrylic hair fixative sold by National Starch.

EXPERIMENTAL RESULTS

Dry Film Characteristics

Both the LV-71 and Example 49 hair spray systems yielded crystal clear hard films after spraying and drying on the glass plate. A clear film is desirable for hair spray systems.

Hair Tress Combability Comparisons

The LV-71 system produced the typical crunchy, stiff feel after spraying and drying on a hair tress. No flaking and good combability was observed with the LV-71 tress. The best combability (ease of combing after spraying and drying) was observed with the composition of Example 49 system. Combability was good after drying.

Curl Retention (93% Relative Humidity)

The amount of curl retention is evaluated by imparting a curl to a hair tress and suspending the tress from one end and allowed to relax in a controlled humidity environment (93% relative humidity). The length of the suspended curl is measured at regular time intervals, and the percent curl retention is determined by the formula $$\% \text{ curl retention} = \frac{L - L_t}{L - L_0} \times 100$$

where L is the original length of the tress
$L_0$ is the length of the tress when the relaxation starts
$L_1$ is the length of the tress at time T.
This test protocol is described by Diaz et al. "Set Relaxation of Human Hair", J. Soc. Cosmet. Chem., 34, 205–212 (July 1983). The best curl retention profile was observed using the composition of Example 49, as demonstrated in the drawing.

DETAILED DESCRIPTION OF THE DRAWING

FIG. 1 shows a curl retention profile of percent curl retention vs. relaxation time. Line A shows curl retention of the control composition comprising LV-71. Line B shows curl retention of Example 49.

What is claimed is:
1. A hair cosmetic composition comprising a graft or block copolymer in an amount of 0.01 to 30% by weight of the composition of the formula

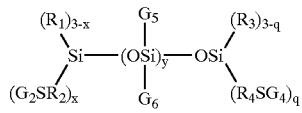

wherein $G_5$ represents monovalent moieties which can independently be the same or different selected from the group consisting of alkyl, aryl, alkaryl, alkoxy, alkylamino, fluoroalkyl, hydrogen, and —ZSA;
A represents a vinyl copolymeric segment consisting essentially of copolymerized free radically copolymerizable monomer,
Z is a divalent linking group;
$G_6$ represents monovalent moieties which can independently be the same or different selected from the group consisting of alkyl, aryl, alkaryl, alkoxy, alkylamino, fluoroalkyl, hydrogen, and —ZSA;
$G_2$ comprises A;
$G_4$ comprises A;
$R_1$ represents monovalent moieties which can independently be the same or different and are selected from the group consisting of alkyl, aryl, alkaryl, alkoxy, alkylamino, fluoroalkyl, hydrogen, and hydroxyl;
$R_2$ can independently be the same or different and represents divalent linking groups;
$R_3$ represents monovalent moieties which can independently be the same or different and are selected from the group consisting of alkyl, aryl, alkaryl, alkoxy, alkylamino, fluoroalkyl, hydrogen, and hydroxyl;
$R_4$ can independently be the same or different and are divalent linking groups;
x is an integer of 0–3;
y is an integer of 5 or greater;
q is an integer of 0–3;
wherein at least one of the following is true:
q is an integer of at least 1;
x is an integer of at least 1;
$G_5$ comprises at least one —ZSA moiety; and
$G_6$ comprises at least one —ZSA moiety,
wherein said hair cosmetic composition is a shampoo, further comprising a surfactant and further,
the balance of said composition comprising one or more compounds chosen from the group of carriers, solvents, preservatives, UV absorbers, anti-oxidants, coloring agents, skin-improvers, humectants, perfumes or vehicle components for a shampoo, wherein said carriers, solvents, preservatives, UV absorbers, anti-oxidants, coloring agents, skin-improvers, humectants, perfumes or vehicle components for a shampoo are chosen so as not to damage or negatively affect the aesthetics of hair or cause irritation to skin.

2. A method for treating hair, which comprises preparing the shampoo of claim 1 and applying said shampoo to the surface of hair.

3. A hair cosmetic composition comprising a graft or block copolymer in an amount of 0.01 to 30% by weight of the composition of the formula

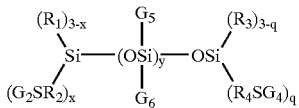

wherein $G_5$ represents monovalent moieties which can independently be the same or different selected from the group consisting of alkyl, aryl, alkaryl, alkoxy, alkylamino, fluoroalkyl, hydrogen, and —ZSA;

A represents a vinyl copolymeric segment consisting essentially of copolymerized free radically copolymerizable monomer, Z is a divalent linking group;

$G_6$ represents monovalent moieties which can independently be the same or different selected from the group consisting of alkyl, aryl, alkaryl, alkoxy, alkylamino, fluoroalkyl, hydrogen, and —ZSA;

$G_2$ comprises A;

$G_4$ comprises A;

$R_1$ represents monovalent moieties which can independently be the same or different and are selected from the group consisting of alkyl, aryl, alkaryl, alkoxy, alkylamino, fluoroalkyl, hydrogen, and hydroxyl;

$R_2$ can independently be the same or different and represents divalent linking groups;

$R_3$ represents monovalent moieties which can independently be the same or different and are selected from the group consisting of alkyl, aryl, alkaryl, alkoxy, alkylamino, fluoroalkyl, hydrogen, and hydroxyl;

$R_4$ can independently be the same or different and are divalent linking groups;

x is an integer of 0–3;

y is an integer of 5 or greater;

q is an integer of 0–3;

wherein at least one of the following is true:
  q is an integer of at least 1;
  x is an integer of at least 1;
  $G_5$ comprises at least one —ZSA moiety; and
  $G_6$ comprises at least one —ZSA moiety,
  wherein said hair cosmetic composition is a hair styling composition,
  the balance of said composition comprising one or more compounds chosen from the group of carriers, solvents, preservatives, UV absorbers, anti-oxidants, coloring agents, skin-improvers, humectants, perfumes or vehicle components for a hair styling composition, wherein said carriers, solvents, preservatives, UV absorbers, anti-oxidants, coloring agents, skin-improvers, humectants, perfumes or vehicle components for a hair styling composition are chosen so as not to damage or negatively affect the aesthetics of hair or cause irritation to skin.

4. A method for treating hair, which comprises preparing the hair styling composition of claim 3 and applying said hair styling composition to the surface of hair.

5. A hair cosmetic composition comprising a graft or block copolymer in an amount of 0.01 to 30% by weight of the composition of the formula

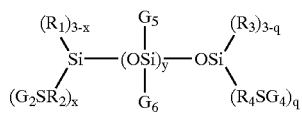

wherein $G_5$ represents monovalent moieties which can independently be the same or different selected from the group consisting of alkyl, aryl, alkaryl, alkoxy, alkylamino, fluoroalkyl, hydrogen, and —ZSA;

A represents a vinyl copolymeric segment consisting essentially of copolymerized free radically copolymerizable monomer, Z is a divalent liking group;

$G_6$ represents monovalent moieties which can independently be the same or different selected from the group consisting of alkyl, aryl, alkaryl, alkoxy, alkylamino, fluoroalkyl, hydrogen, and —ZSA;

$G_2$ comprises A;

$G_4$ comprises A;

$R_1$ represents monovalent moieties which can independently be the same or different and are selected from the group consisting of alkyl, aryl, alkaryl, alkoxy, alkylamino, fluoroalkyl, hydrogen, and hydroxyl;

$R_2$ can independently be the same or different and represents divalent linking groups;

$R_3$ represents monovalent moieties which can independently be the same or different and are selected from the group consisting of alkyl, aryl, alkaryl, alkoxy, alkylamino, fluoroalkyl, hydrogen, and hydroxyl;

$R_4$ can independently be the same or different and are divalent linking groups;

x is an integer of 0–3;

y is an integer of 5 or greater;

q is an integer of 0–3;

wherein at least one of the following is true:
  q is an integer of at least 1;
  x is an integer of at least 1;
  $G_5$ comprises at least one —ZSA moiety; and
  $G_6$ comprises at least one —ZSA moiety,
  wherein said hair cosmetic composition is a mousse, tonic, spray or gel,
  the balance of said composition comprising one or more compounds chosen from the group of carriers, solvents, preservatives, UV absorbers, anti-oxidants, coloring agents, skin-improvers, humectants, perfumes or vehicle components for a mousse, tonic, spray or gel, wherein said carriers, solvents, preservatives, UV absorbers, anti-oxidants, coloring agents, skin-improvers, humectants, perfumes or vehicle components for a mousse, tonic, spray or gel are chosen so as not to damage or negatively affect the aesthetics of hair or cause irritation to skin.

6. A method for treating hair, which comprises preparing the mouse, tonic, spray or gel of claim 5 and applying said mouse, tonic, spray or gel to the surface of hair.

7. A hair cosmetic composition comprising a graft or block copolymer in an amount of 0.01 to 30% by weight of the composition of the formula

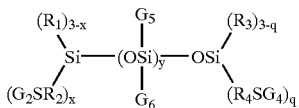

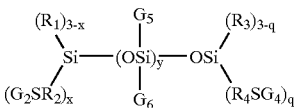

wherein $G_5$ represents monovalent moieties which can independently be the same or different selected from the group consisting of alkyl, aryl, alkaryl, alkoxy, alkylamino, fluoroalkyl, hydrogen, and —ZSA;

A represents a vinyl copolymeric segment consisting essentially of copolymerized free radically copolymerizable monomer, Z is a divalent linking group;

$G_6$ represents monovalent moieties which can independently be the same or different selected from the group consisting of alkyl, aryl, alkaryl, alkoxy, alkylamino, fluoroalkyl, hydrogen, and —ZSA;

$G_2$ comprises A;

$G_4$ comprises A;

$R_1$ represents monovalent moieties which can independently be the same or different and are selected from the group consisting of alkyl, aryl, alkaryl, alkoxy, alkylamino, fluoroalkyl, hydrogen, and hydroxyl;

$R_2$ can independently be the same or different and represents divalent linking groups;

$R_3$ represents monovalent moieties which can independently be the same or different and are selected from the group consisting of alkyl, aryl, alkaryl, alkoxy, alkylamino, fluoroalkyl, hydrogen, and hydroxyl;

$R_4$ can independently be the same or different and are divalent linking groups;

x is an integer of 0–3;

y is an integer of 5 or greater;

q is an integer of 0–3;

wherein at least one of the following is true:
q is an integer of at least 1;
x is an integer of at least 1;
$G_5$ comprises at least one —ZSA moiety; and
$G_6$ comprises at least one —ZSA moiety,
wherein said hair cosmetic composition is a rinse or hair treatment,
the balance of said composition comprising one or more compounds chosen from the group of carriers, solvents, preservatives, UV absorbers, anti-oxidants, coloring agents, skin-improvers, humectants, perfumes or vehicle components for a rinse or hair treatment, wherein said carriers, solvents, preservatives, UV absorbers, anti-oxidants, coloring agents, skin-improvers, humectants, perfumes or vehicle components for a rinse or hair treatment are chosen so as not to damage or negatively affect the aesthetics of hair or cause irritation to skin.

8. A method for treating hair, which comprises preparing the rinse or hair treatment of claim 7 and applying said rinse or hair treatment to the surface of hair.

9. A hair cosmetic composition comprising a graft or block copolymer in an amount of 0.01 to 30% by weight of the composition of the formula wherein $G_5$ represents monovalent moieties which can independently be the same or different selected from the group consisting of alkyl, aryl, alkaryl, alkoxy, alkylamino, fluoroalkyl, hydrogen, and —ZSA;

A represents a vinyl copolymeric segment consisting essentially of copolymerized free radically copolymerizable monomer, Z is a divalent linking group;

$G_6$ represents monovalent moieties which can independently be the same or different selected from the group consisting of alkyl, aryl, alkaryl, alkoxy, alkylamino, fluoroalkyl, hydrogen, and —ZSA;

$G_2$ comprises A;

$G_4$ comprises A;

$R_1$ represents monovalent moieties which can independently be the same or different and are selected from the group consisting of alkyl, aryl, alkaryl, alkoxy, alkylamino, fluoroalkyl, hydrogen, and hydroxyl;

$R_2$ can independently be the same or different and represents divalent linking groups;

$R_3$ represents monovalent moieties which can independently be the same or different and are selected from the group consisting of alkyl, aryl, alkaryl, alkoxy, alkylamino, fluoroalkyl, hydrogen, and hydroxyl;

$R_4$ can independently be the same or different and are divalent linking groups;

x is an integer of 0–3;

y is an integer of 5 or greater;

q is an integer of 0–3;

wherein at least one of the following is true:
q is an integer of at least 1;
x is an integer of at least 1;
$G_5$ comprises at least one —ZSA moiety; and
$G_6$ comprises at least one —ZSA moiety,
wherein said hair cosmetic composition is a hair setting preparation,
the balance of said composition comprising one or more compounds chosen from the group of carriers, solvents, preservatives, UV absorbers, anti-oxidants, coloring agents, skin-improvers, humectants, perfumes or vehicle components for a hair setting preparation, wherein said carriers, solvents, preservatives, U absorbers, anti-oxidants, coloring agents, skin-improvers, humectants, perfumes or vehicle components for a hair setting preparation are chosen so as not to damage or negatively affect the aesthetics of hair or cause irritation to skin.

10. A method for treating hair, which comprises preparing the hair setting preparation of claim 9 and applying said hair setting preparation to the surface of hair.

11. A hair cosmetic composition comprising a graft or block copolymer in an amount of 0.01 to 30% by weight of the composition of the formula

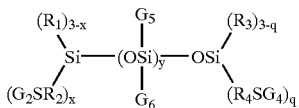

wherein $G_5$ represents monovalent moieties which can independently be the same or different selected from the group consisting of alkyl, aryl, alkaryl, alkoxy, alkylamino, fluoroalkyl, hydrogen, and —ZSA;

A represents a vinyl copolymeric segment consisting essentially of copolymerized free radically copolymerizable monomer, Z is a divalent linking group;

$G_6$ represents monovalent moieties which can independently be the same or different selected from the group consisting of alkyl, aryl, alkaryl, alkoxy, alkylamino, fluoroalkyl, hydrogen, and —ZSA;

$G_2$ comprises A;

$G_4$ comprises A;

$R_1$ represents monovalent moieties which can independently be the same or different and are selected from the group consisting of alkyl, aryl, alkaryl, alkoxy, alkylamino, fluoroalkyl, hydrogen, and hydroxyl;

$R_2$ can independently be the same or different and represents divalent linking groups;

$R_3$ represents monovalent moieties which can independently be the same or different and are selected from the group consisting of alkyl, aryl, alkaryl, alkoxy, alkylamino, fluoroalkyl, hydrogen, and hydroxyl;

$R_4$ can independently be the same or different and are divalent linking groups;

x is an integer of 0–3;

y is an integer of 5 or greater;

q is an integer of 0–3;

wherein at least one of the following is true:
q is an integer of at least 1;
x is an integer of at least 1;
$G_5$ comprises at least one —ZSA moiety; and
$G_6$ comprises at least one —ZSA moiety,
wherein said hair cosmetic composition is a permanent wave lotion,
the balance of said composition comprising one or more compounds chosen from the group of carriers, solvents, preservatives, UV absorbers, anti-oxidants, coloring agents, skin-improvers, humectants, perfumes or vehicle components for a permanent wave lotion, wherein said carriers, solvents, preservatives, UV absorbers, anti-oxidants, coloring agents, skin-improvers, humectants, perfumes or vehicle components for a permanent wave lotion are chosen so as not to damage or negatively affect the aesthetics of hair or cause irritation to skin.

12. A method for treating hair, which comprises preparing the permanent wave lotion of claim 11 and applying said permanent wave lotion to the surface of hair.

13. A hair cosmetic composition comprising a graft or block copolymer in an amount of 0.01 to 30% by weight of the composition of the formula

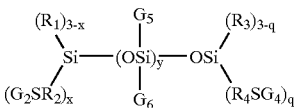

wherein $G_5$ represents monovalent moieties which can independently be the same or different selected from the group consisting of alkyl, aryl, alkaryl, alkoxy, alkylamino, fluoroalkyl, hydrogen, and —ZSA;

A represents a vinyl copolymeric segment consisting essentially of copolymerized free radically copolymerizable monomer, Z is a divalent linking group;

$G_6$ represents monovalent moieties which can independently be the same or different selected from the group consisting of alkyl, aryl, alkaryl, alkoxy, alkylamino, fluoroalkyl, hydrogen, and —ZSA;

$G_2$ comprises A;

$G_4$ comprises A;

$R_1$ represents monovalent moieties which can independently be the same or different and are selected from the group consisting of alkyl, aryl, alkaryl, alkoxy, alkylamino, fluoroalkyl, hydrogen, and hydroxyl;

$R_2$ can independently be the same or different and represents divalent linking groups;

$R_3$ represents monovalent moieties which can independently be the same or different and are selected from the group consisting of alkyl, aryl, alkaryl, alkoxy, alkylamino, fluoroalkyl, hydrogen, and hydroxyl;

$R_4$ can independently be the same or different and are divalent linking groups;

x is an integer of 0–3;

y is an integer of 5 or greater;

q is an integer of 0–3;

wherein at least one of the following is true:
q is an integer of at least 1;
x is an integer of at least 1;
$G_5$ comprises at least one —ZSA moiety; and
$G_6$ comprises at least one —ZSA moiety,
the balance of said composition comprising one or more compounds chosen from the group of carriers, solvents, preservatives, UV absorbers, anti-oxidants, coloring agents, skin-improvers, humectants, perfumes or vehicle components for a hair cosmetic composition, wherein said carriers, solvents, preservatives, UV absorbers, anti-oxidants, coloring agents, skin-improvers, humectants, perfumes or vehicle components for a hair cosmetic composition are chosen so as not to damage or negatively affect the aesthetics of hair or cause irritation to skin.

14. The hair cosmetic composition of claim 13, wherein $R_1$ is selected from the group consisting of $C_{1-4}$ alkyl and hydroxyl.

15. The hair cosmetic composition of claim 13, wherein $R_2$ is selected from the group consisting of $C_1$ to $C_{10}$ alkylene, arylene, alkarylene, and alkoxyalkylene.

16. The hair cosmetic composition of claim 13, wherein $R_3$ is selected from the group consisting of $C_{1-4}$ alkyl and hydroxyl.

17. The hair cosmetic composition of claim 13, wherein $R_4$ is selected from the group consisting of $C_1$ to $C_{10}$ alkylene, arylene, alkarylene and alkoxyalkylene.

18. The hair cosmetic composition of claim 13, wherein Z is selected from the group consisting of $C_1$ to $C_{10}$ alkylene, alkarylene, arylene, and alkoxyalkylene.

19. The hair cosmetic composition of claim 13, wherein $G_5$ is selected from the group consisting of $C_{1-3}$ alkyl, fluoroalkyl, and phenyl.

20. The hair cosmetic composition of claim 13, wherein $G_6$ is selected from the group consisting of $C_{1-3}$ alkyl, fluoroalkyl, and phenyl.

21. The hair cosmetic composition of claim 13, wherein y is an integer ranging from about 10 to about 270.

22. The hair cosmetic composition of claim 13, wherein y is an integer ranging from about 40 to about 270.

23. The hair cosmetic composition of claim 13, wherein A comprises copolymerized free radically copolymerizable monomer selected from the group consisting of acrylic acid esters of alkyl alcohols having from 1 to 18 carbon atoms and methacrylic acid esters of alcohols selected from the group consisting of alkyl alcohols having from 1 to 18 carbon atoms.

24. The hair cosmetic composition of claim 23, wherein A further comprises copolymerized free radically copolymerizable monomer selected from the group consisting of acrylic acid, methacrylic acid, itaconic acid, acrylonitrile, crotonic acid, acrylamide, N,N dimethylacrylamide, N-t-butylacrylamide and methacrylonitrile.

25. The hair cosmetic composition of claim 13, wherein A comprises copolymerized free radically copolymerizable monomer selected from the group consisting of acrylic acid esters of alkyl alcohols having from 1 to 8 carbon atoms and methacrylic acid esters of alkyl alcohols having from 1 to 8 carbon atoms.

26. The hair cosmetic composition of claim 13, wherein A comprises copolymerized free radically copolymerizable monomer selected from the group consisting of isooctyl (meth)acrylate, lauryl (meth)acrylate, 2-ethylhexyl (meth)acrylate, isononyl (meth)acrylate, i-pentyl (meth)acrylate, n-butyl (meth)acrylate, i-butyl (meth)acrylate, methyl (meth)acrylate, ethyl (meth)acrylate, t-butyl(meth)acrylate, stearyl (meth)acrylate and mixtures thereof.

27. The hair cosmetic composition of claim 13, wherein A comprises copolymerized free radically copolymerizable hydrophilic unsaturated monomer selected from the group consisting of cationic, anionic, nonionic, and amphoteric monomers.

28. The hair cosmetic composition of claim 13, wherein A comprises copolymerized free radically copolymerizable monomer selected from the group consisting of acrylic acid, methacrylic acid, itaconic acid, acrylonitrile, crotonic acid, acrylamide, N,N-dimethylacrylamide, N-t-butylacrylamide and methacrylonitrile.

29. The hair cosmetic composition of claim 13, wherein A comprises copolymerized free radically copolymerizable monomer selected from the group consisting of half esters of succinic anhydride or phthalic anhydride with hydroxy ethyl (meth)acrylate or hydroxy propyl (meth)acryate.

30. The hair cosmetic composition of claim 13, wherein A comprises copolymerized free radically copolymerizable monomer selected from the group consisting of poly (styrene), poly(a-methyl styrene), poly(vinyltoluene), poly (oxyalkylene) and polymethyl(meth)acrylate macromonomers.

31. The hair cosmetic composition of claim 13, wherein A comprises copolymerized free radically copolymerizable monomer selected from the group consisting of acrylic and methacrylic monomers, wherein said monomers have at least one polar group selected from the group consisting of hydroxyl, primary amine, secondary amine, tertiary amine, and ionic groups.

32. The hair cosmetic composition of claim 13, wherein A comprises copolymerized free radically copolymerizable monomer selected from the group consisting of monomers represented by the formula:

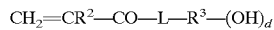

where $R^2$=H, methyl, ethyl, cyano or carboxymethyl, L=—O, —NH, d=1–3 and $R^3$ is a hydrocarbyl radical of valence d+1 containing from 1 to 12 carbon atoms.

33. The hair cosmetic composition of claim 13, wherein A comprises copolymerized free radically copolymerizable monomer selected from the group consisting of hydroxyethyl (meth)acrylate, hydroxypropyl(meth)acrylate, hydroxybutyl (meth)acrylate, glycerol mono(meth)acrylate, tris(hydroxymethyl) ethane monoacrylate, pentaerythritol mono(meth)acrylate, N-hydroxymethyl (meth)acrylamide, hydroxyethyl (meth)acrylamide and hydroxypropyl (meth)acrylamide.

34. The hair cosmetic composition of claim 13, wherein A comprises copolymerized free radically copolymerizable monomer selected from the group consisting of monomers of the formula:

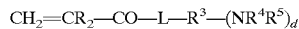

where
$R_2$=H, methyl, ethyl, cyano or carboxymethyl,
L=—O, —NH
d=1–3,
$R^3$ is a hydrocarbyl radical of valence d+1 containing from 1 to 12 carbon atoms, and $R^4$ and $R^5$ are H or alkyl groups of 1 to 12 carbon atoms or together constitute a carbocyclic or heterocyclic group.

35. The hair cosmetic composition of claim 13, wherein A comprises copolymerized free radically copolymerizable monomer selected from the group consisting of aminoethyl (meth) acrylate, aminopropyl (meth)acrylate, N,N-dimethylaminoethyl (meth)acrylate, N,N-diethylaminoethyl (meth)acrylate, N,N-dimethylaminopropyl (meth) acrylamide, N-isopropylaminopropyl (meth)acrylamide, and 4-methyl-1-acryloyl-piperazine.

36. The hair cosmetic composition of claim 13, wherein A comprises a copolymerized free radically copolymerizable monomer of the formula:

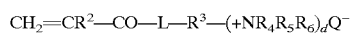

where
$R_2$=H, methyl, ethyl, cyano or carboxymethyl,
L=—O, —NH,
d=1–3,
$R^3$ is a hydrocarbyl radical of valence d+1 containing from 1 to 12 carbon atoms,
and $R^4$ and $R^5$ are H or alkyl groups of 1 to 12 carbon atoms or together constitute a carbocyclic or heterocyclic group,
$R^6$ is H or alkyl group of 1–12 carbon atoms, and $Q^-$ is an organic or inorganic anion.

37. The hair cosmetic composition of claim 13, wherein A comprises copolymerized free radically copolymerizable monomer selected from the group consisting of 2-N,N,N-trimethylammonium ethyl (meth)acrylate, 2-N,N,N-triethylammonium ethyl (meth)acrylate, 3-N,N,N-triethylammonium propyl (meth)acrylate, N(2-N',N',N'-trimethylammonium) ethyl (meth)acrylamide and N-(dimethylhydroxyethylammonium) propyl (meth) acrylamide.

38. The hair cosmetic composition of claim 37, wherein the monomer has a counterion selected from the group consisting of chloride, bromide, acetate, propionate, laurate, palmitate and stearate.

39. The hair cosmetic composition of claim 13, wherein A comprises copolymerized free radically copolymerizable monomer selected from the group consisting of methoxyethyl (meth)acrylate, 2(2-ethoxyethoxy)ethyl (meth) acrylate, polyethylene glycol mono(meth)acrylate and polypropylene glycol mono(meth)acrylate.

40. The hair cosmetic composition of claim 13, wherein A comprises copolymerized free radically copolymerizable monomer selected from the group consisting of vinyl sulphonic acid, styrene sulphonic acid, 2-acrylamido-2-methyl propane sulphonic acid and allyloxybenzene sulphonic acid.

41. The hair cosmetic composition of claim 13, wherein A comprises copolymerized free radically copolymerizable monomer selected from the group consisting of vinyl pyridines, vinyl imidazoles, vinyl benzimidazoles, vinyl azlactones, N-vinyl pyrrolidone and vinyl furans.

42. The hair cosmetic composition of claim 13, wherein $G_5$, $R_1$, and $R_2$ are each methyl, x and q are each 0, y is 40 to about 270, $G_6$ is methyl or —ZSA where Z is selected from the group consisting of $C_1$ to $C_{10}$ alkylene, alkarylene, arylene, and alkoxyalkylene, and A comprises copolymerized isobutyl methacrylate.

43. The hair cosmetic composition of claim 13, wherein $G_5$, $R_1$, and $R_2$ are each methyl, x and q are each 0, y is 40 to about 270, $G_6$ is methyl or —ZSA where Z is selected from the group consisting of $C_1$ to $C_{10}$ alkylene, alkarylene, arylene, and alkoxyalkylene, and A comprises copolymerized free radically copolymerizable monomer selected from the group consisting of methyl methacylate, methyl acrylate, methacrylic acid, and mixtures thereof.

44. The hair cosmetic composition of claim 13, wherein said copolymer is the reaction product of
a) 5–40 weight percent of a mercapto-functional silicone compound of the formula

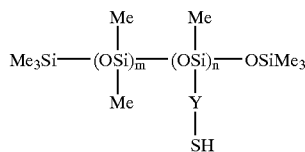

wherein the mole ratio of m/n is 9–49, Y is selected from $C_{1-10}$ alkylene and alkarylene having at least 10 carbons, wherein the bracketed groups may be randomly distributed throughout the compound, said compound having a total number average molecular weight of 350–20,000;
b) 0–25 weight percent of a free radically copolymerizable soft monomer; and
c) 35–95 weight percent of a free radically copolymerizable hard monomer;
said b) and c) components forming a vinyl portion of said copolymer; wherein the glass transition temperature of the vinyl portion of the copolymer is about 60°–110° C.

45. The hair cosmetic composition of claim 44, wherein the glass transition temperature of the vinyl portion of the copolymer is about 80°–100° C.

46. The hair cosmetic composition of claim 44, wherein said mercapto-functional silicone compound has a total number average molecular weight of 4,000–15,000.

47. The hair cosmetic composition of claim 44, wherein said mercapto-functional silicone compound has a total number average molecular weight of 8,000–12,000.

48. The hair cosmetic composition of claim 44, wherein said mercapto-functional silicone compound has a mole ratio of n/n of 15–25.

49. The hair cosmetic composition of claim 44, wherein the mercapto-functional silicone comprises 20–35 weight percent of the copolymer.

50. The hair cosmetic composition of claim 44, wherein the soft monomer is selected from the group consisting of the esters of acrylic acid with methanol, ethanol, 1-propanol, 2-propanol, 2-methyl-1-propanol, 1-butanol, 2-butanol, 1-pentanol, 2-pentanol, 3-pentanol, 2-methyl-1-butanol, 1-hexanol, 2-hexanol, 2-methyl-1-pentanol, 3-methyl-1-pentanol, 2-ethyl-1 butanol, 3,5,5-trimethyl-1-hexanol, 3-heptanol, 1-octanol, 2-octanol, iso-octyl alcohol, 2-ethyl-1-hexanol, 1-decanol, 1-dodecanol, 1-tridecanol, 1-tetradecanol, and the esters of methacrylic acid with 3-heptanol, 1-octanol, 2-octanol, iso-octyl alcohol, 2-ethyl-1-hexanol, 1-decanol, 1-dodecanol, 1-tridecanol, 1-tetradecanol, 1-octadecanol, and mixtures thereof.

51. The hair cosmetic composition of claim 44, wherein the soft monomer is selected from the group consisting of methyl acrylate and ethyl acrylate.

52. The hair cosmetic composition of claim 44, wherein the hard monomer is selected from the group consisting of acrylic acid, methacrylic acid, or monomeric acid esters of methacrylic acid with methanol, ethanol, 1-propanol, 2-propanol, 1,1-dimethyl ethanol, 1-butanol, 2-butanol, 1-pentanol, 2-pentanol, 3-pentanol, and mixtures thereof.

53. The hair cosmetic composition of claim 44, wherein the hard monomer is selected from the group consisting of methyl methacrylate, ethyl methacrylate, isobutyl methacrylate, tertiary butyl acrylate, isobornyl acrylate and isobornyl methacrylate.

54. The hair cosmetic composition of claim 44, wherein said copolymer is the reaction product of
a) 20–35 weight percent of the mercapto-functional silicone compound wherein the mole ratio of m/n is 15–25 and the total number average molecular weight is 8,000 to 12,000;
b) 0 weight percent of the free radically copolymerizable soft monomer; and
c) 65–80 weight percent of isobutyl methacrylate.

55. The hair cosmetic composition of claim 44, wherein said copolymer is the reaction product of
a) 20–35 weight percent of the mercapto-functional silicone compound wherein the mole ratio of m/n is 15–25 and the total average molecular weight is 8,000 to 12,000;
b) 15–25 weight percent methyl acrylate; and
c) a mixture of 45–55 weight percent methyl methacrylate and 5–15 weight percent methacrylic acid.

* * * * *

UNITED STATES PATENT AND TRADEMARK OFFICE
CERTIFICATE OF CORRECTION

PATENT NO. : 6,562,324 B1
DATED : May 13, 2003
INVENTOR(S) : Kanta Kumar et al.

It is certified that error appears in the above-identified patent and that said Letters Patent is hereby corrected as shown below:

Column 38,
Line 19, "liking" should read -- linking --.
Lines 63 and 64, "mouse," should read -- mousse, --.

Column 40,
Line 56, "U absorbers," should read -- UV absorbers, --.

Column 43,
Line 52, "propyl (meth)acryate." should read -- propyl (meth)acrylate. --.

Column 44,
Line 22, "$CH_2=CR_2-CO-L-R^3-(NR^4R^5)_d$" should read
-- $CH_2=CR^2-CO-L-R^3-(NR^4R^5)_d$ --.
Line 25, "$R_2=H$," should read -- $R^2=H$, --.
Line 44, "$CH_2=CR^2-CO-L-R^3-(+NR_4R_5R_6)_dQ^-$" should read
-- $CH_2=CR^2-CO-L-R^3-(^+NR^4R^5R^6)_dQ^-$ --.
Line 46, "$R_2=H$," should read -- $R^2=H$, --.

Column 45,
Line 30, "methyl methacylate," should read -- methyl methacrylate --.

Column 46,
Line 6, "ratio of n/n" should read -- ratio of m/n --.
Line 39, "isobomyl" should read -- isobornyl --.

Signed and Sealed this

Fifteenth Day of July, 2003

JAMES E. ROGAN
*Director of the United States Patent and Trademark Office*